United States Patent [19]
Masterson et al.

[11] Patent Number: 5,518,686
[45] Date of Patent: May 21, 1996

[54] SPECIMEN PROCESSING AND ANALYZING SYSTEMS WITH ASSOCIATED FLUID DISPENSING APPARATUS

[75] Inventors: Brian K. Masterson, Placerville; Randolph L. Campbell, Sacramento; Craig M. Daniel, El Dorado Hills, all of Calif.

[73] Assignee: Dade MicroScan Inc., W. Sacramento, Calif.

[21] Appl. No.: 270,728

[22] Filed: Jul. 5, 1994

Related U.S. Application Data

[63] Continuation of Ser. No. 786,184, Oct. 31, 1991, abandoned.

[51] Int. Cl.$^6$ .......................... G01N 35/04; G01N 35/06
[52] U.S. Cl. .................. 422/63; 422/64; 422/65; 422/100; 422/103; 435/287.3; 436/45; 436/47; 141/130; 414/223
[58] Field of Search .............................. 422/63–67, 68.1, 422/100, 103–104; 198/803.14, 478.1, 608, 345.1, 345.3; 436/45, 47, 54; 435/292; 222/504, 511; 141/130, 236; 414/223, 225, 751; 239/285; 403/DIG. 1, 404, 328

[56] References Cited

U.S. PATENT DOCUMENTS

| | | | |
|---|---|---|---|
| 1,906,723 | 5/1933 | Rosendahl | 312/270.3 |
| 1,998,343 | 4/1935 | Teller et al. | 312/308 |
| 3,240,390 | 3/1966 | Mitchell et al. | 222/504 |
| 3,606,513 | 9/1971 | Hoffmann et al. | 312/351 |
| 3,772,154 | 11/1973 | Isenberg et al. | 435/292 |
| 3,912,456 | 10/1975 | Young | 436/47 |
| 4,118,280 | 10/1978 | Charles et al. | 422/102 |
| 4,517,160 | 5/1985 | Galle et al. | 422/65 |
| 4,574,225 | 3/1986 | Pershall et al. | 318/254 |
| 4,602,890 | 7/1986 | Duda | 403/105 |
| 4,639,163 | 1/1987 | Buthe et al. | 403/322 |
| 4,643,879 | 2/1987 | Hanaway | 422/104 |
| 4,676,951 | 6/1987 | Armes et al. | 422/65 |
| 4,681,741 | 7/1987 | Hanaway | 422/100 |
| 4,710,690 | 12/1987 | Reid et al. | 318/685 |
| 4,803,050 | 2/1989 | Mack | 422/65 |
| 4,871,290 | 10/1989 | Kaczynski et al. | 414/331 |
| 4,930,640 | 6/1990 | Edwards | 211/41 |
| 4,933,621 | 6/1990 | MacMinn et al. | 318/696 |
| 4,940,452 | 7/1990 | Rohe | 600/7 |
| 5,032,780 | 7/1991 | Hopkins | 318/696 |
| 5,094,516 | 3/1992 | Hunter | 312/319 |

FOREIGN PATENT DOCUMENTS 193385  9/1986  European Pat. Off. .

OTHER PUBLICATIONS

International Search Report relative to PCT International Application No. PCT/US92/09098.

Primary Examiner—Robert J. Warden
Assistant Examiner—Hien Tran
Attorney, Agent, or Firm—Terry L. Miller

[57] ABSTRACT

A system for processing a specimen to which fluid must be added includes a fluid dispensing work station within a housing. The work station holds the fluids that are to be added to the specimen. A nozzle dispenses fluid at the work station. The system also includes a carrier that moves within the housing. The carrier operates in a first mode at the fluid dispensing work station. The carrier also operates in a second mode outside the work station to perform a different processing function. A coupling mechanism attaches the nozzle to the carrier when the carrier enters its first operational mode to transport the nozzle around the fluid dispensing station. The coupling mechanism releases the nozzle from the carrier when the carrier enters its second operational mode, thereby freeing the carrier for movement outside the work station out of association with the nozzle.

33 Claims, 23 Drawing Sheets

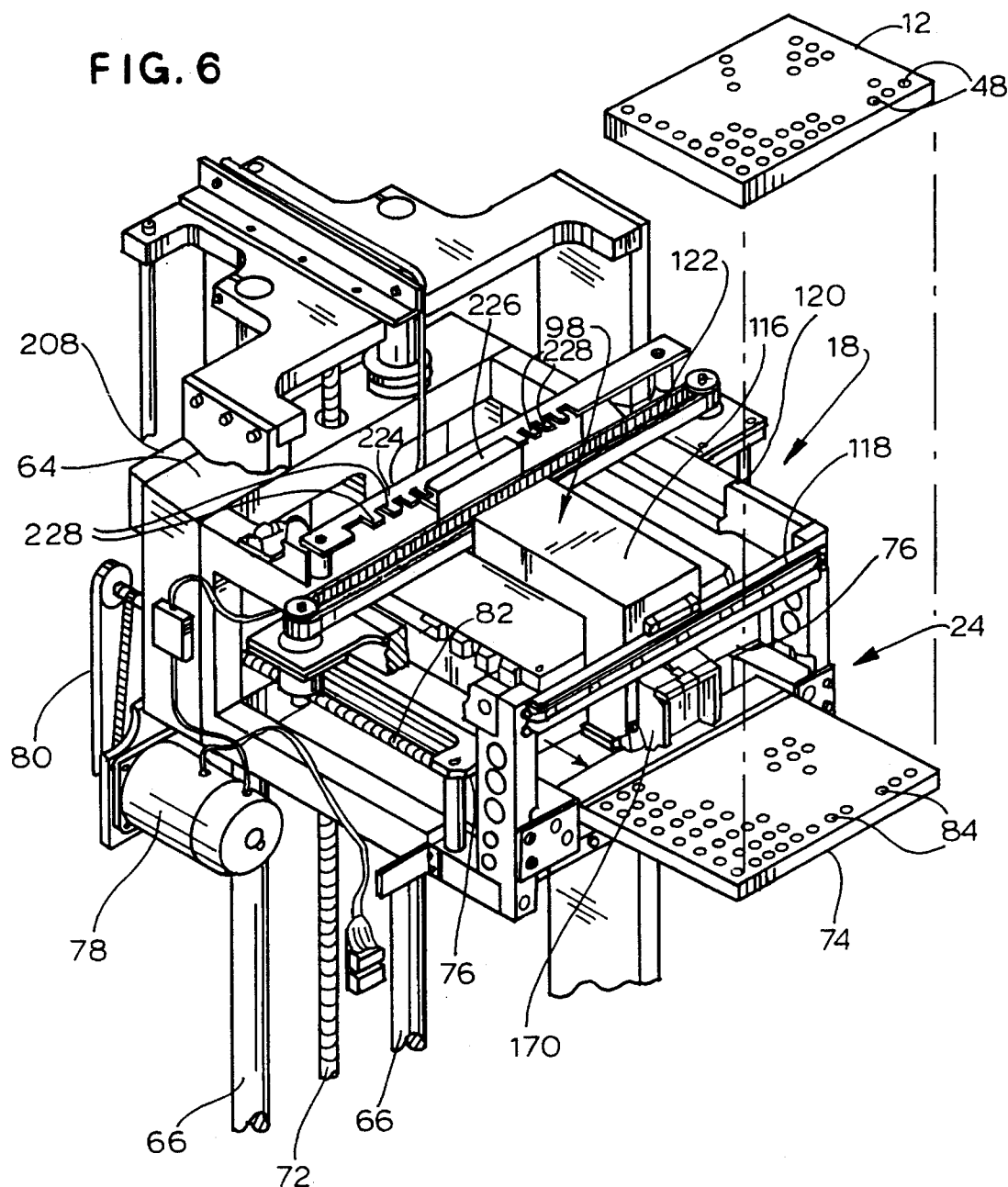

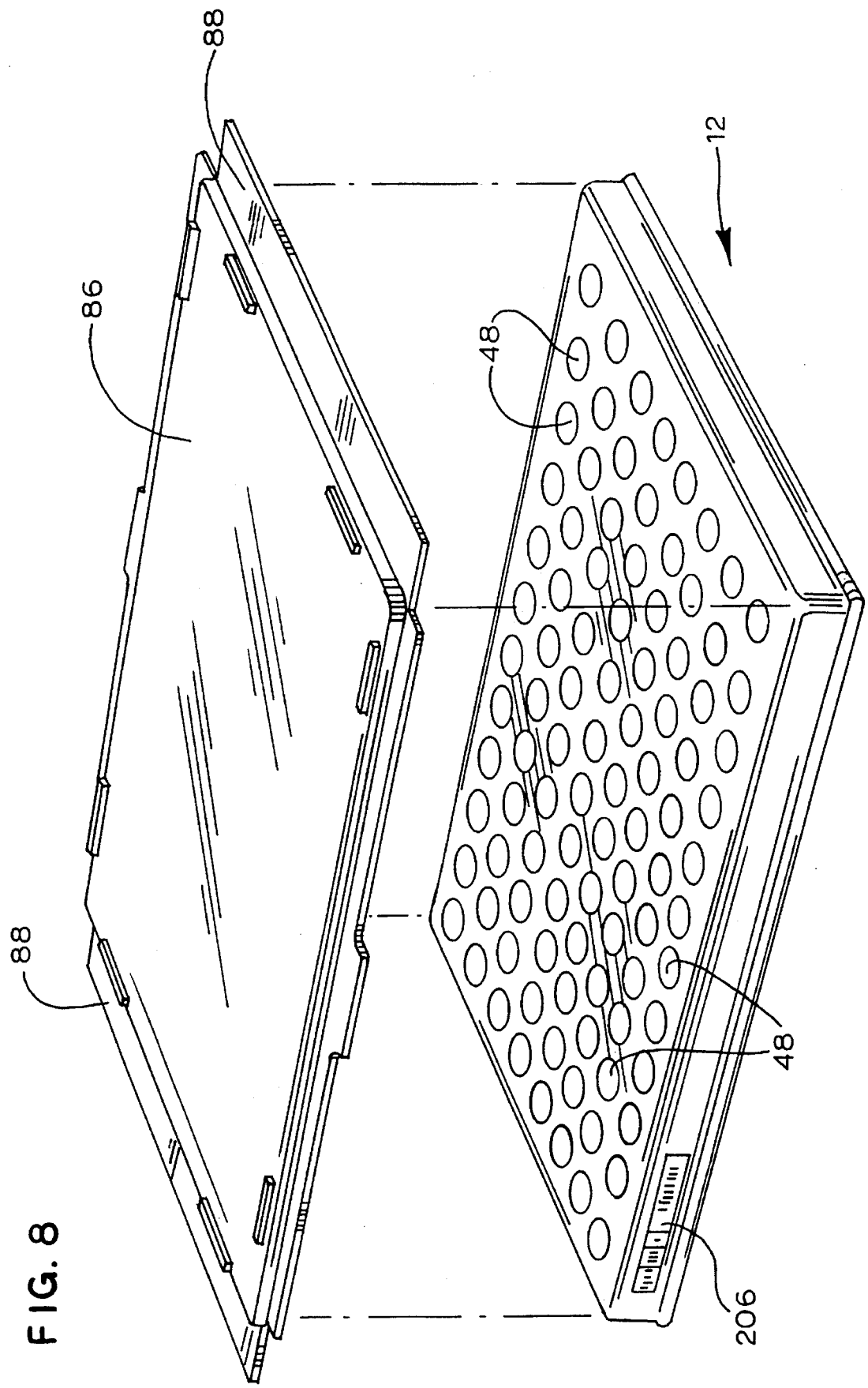

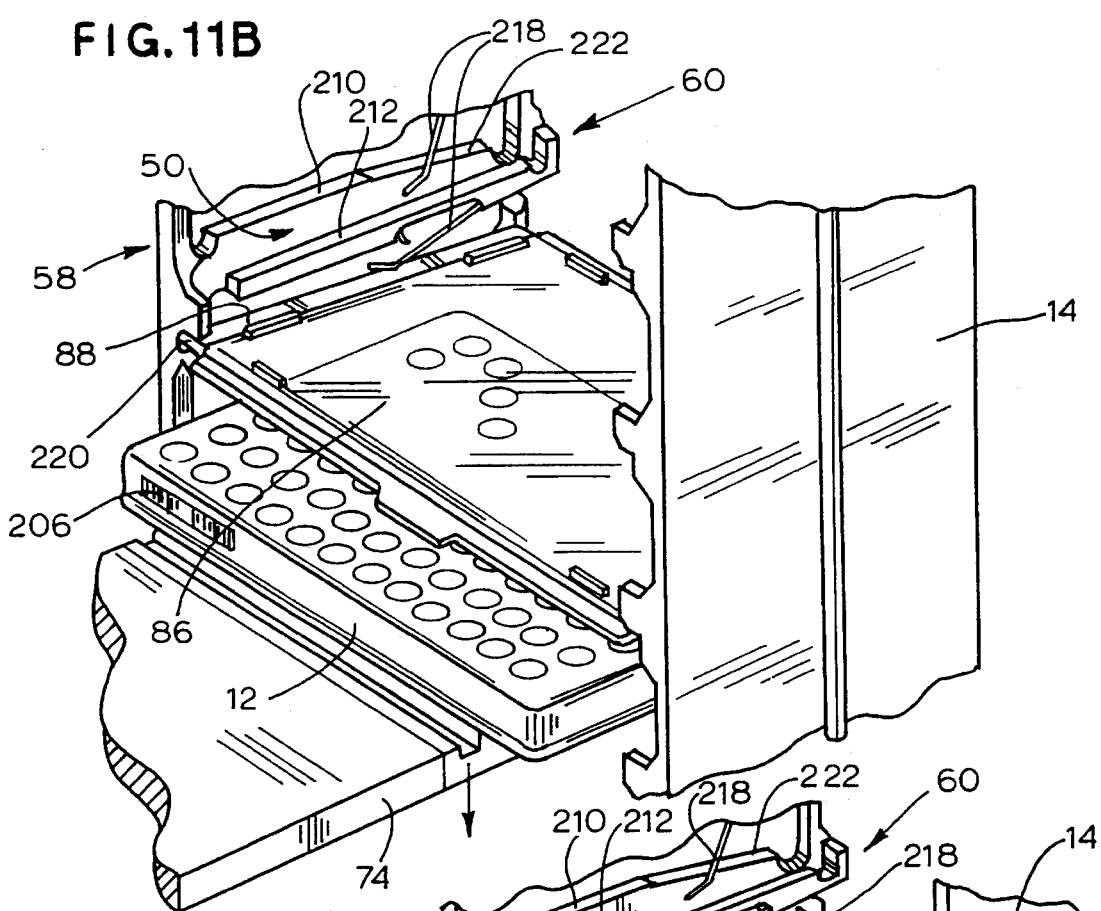
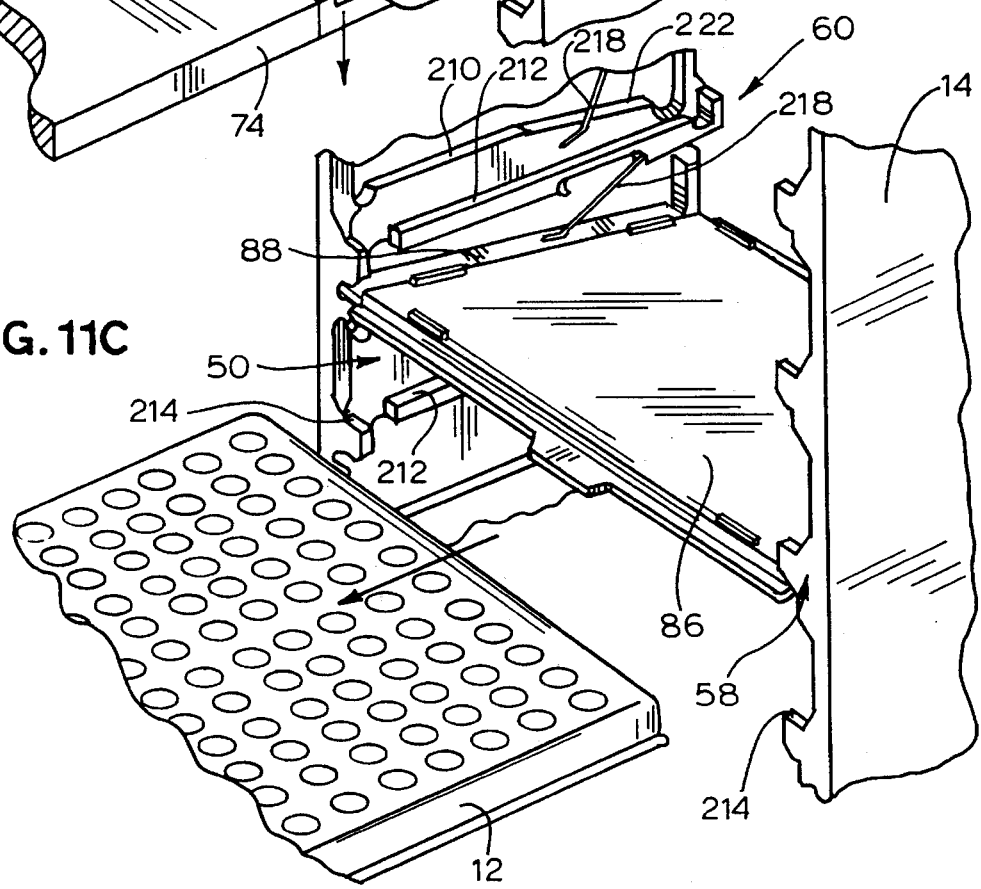

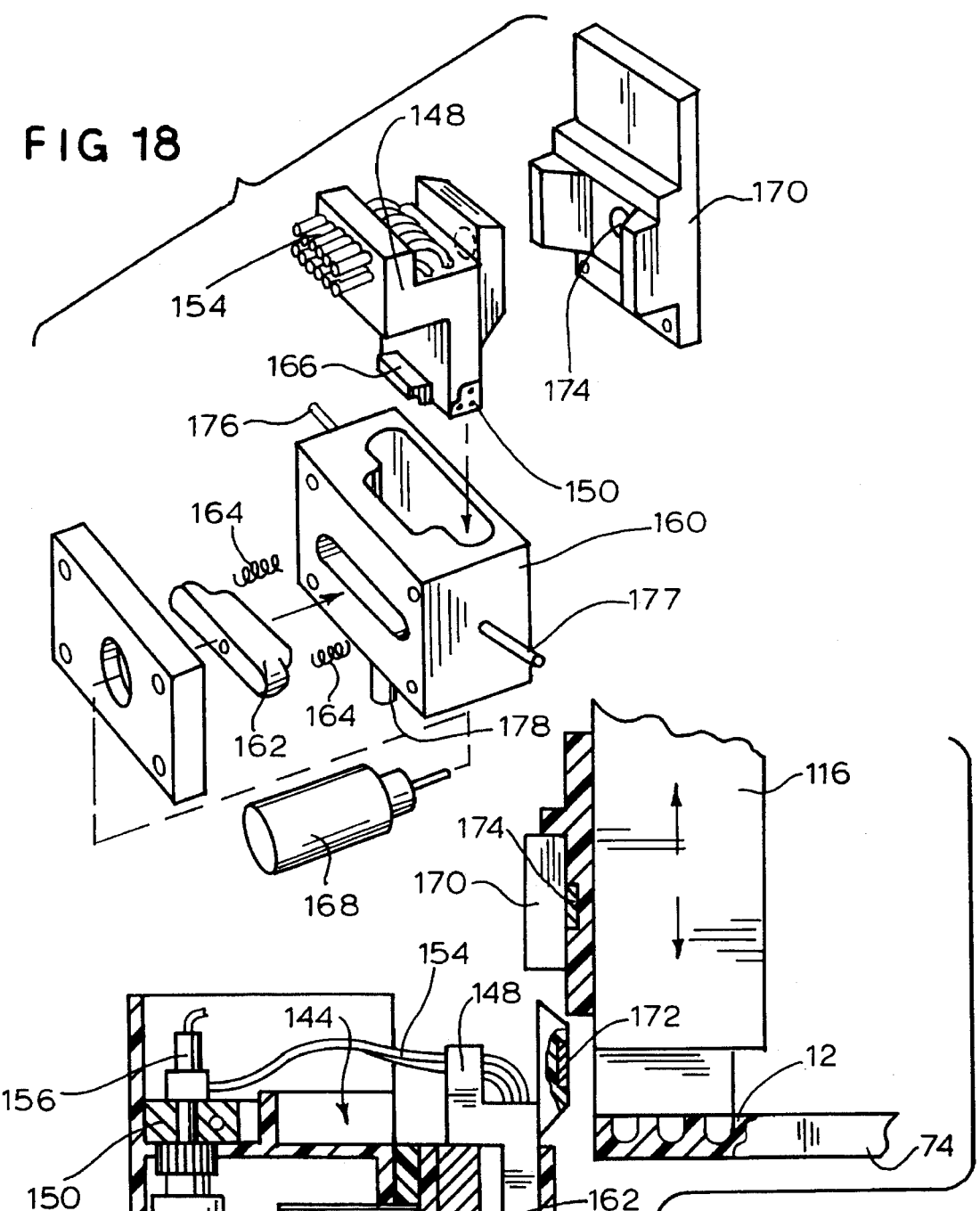

SPECIMEN PROCESSING AND ANALYZING SYSTEMS WITH ASSOCIATED FLUID DISPENSING APPARATUS

This is a continuation of copending patent application(s) Ser. No. 07/786,184 filed on Oct. 31, 1991, now abandoned.

FIELD OF THE INVENTION

The invention relates to analytical systems used in different environments to carry out analytical, laboratory, and clinical procedures.

BACKGROUND OF THE INVENTION

There are conventional devices that carry out multi-step analytical procedures in an automated or semi-automated fashion. For example, microbiological analytical systems currently carry out automated antimicrobic susceptibility testing procedures using both photometric and fluorometric detection methods. The MicroScan Division of Baxter Healthcare Corporation sells a device of this type under the trade designation "Walk-Away." Armes et al. U.S. Pat. No. 4,676,951 and Hanaway U.S. Pat. Nos. 4,643,879 and 4,681,741 describe certain features the Walk-Away system.

Prior commercial embodiments of the Walk-Away system analyze trays carrying microbiologic specimens. The system includes an enclosed incubation chamber for the specimens. The system adds reagents to the specimens and analyzes them. All these activities take place within the incubation chamber.

Prior commercial embodiments of the Walk-Away system house the reagent fluids outside the incubation area. The system conveys these fluids under positive pressure through relatively long stretches of tubing leading from the reagent source to the incubation area. A mechanism within the incubation area manipulates the nozzle that dispenses the reagents.

Prior commercial embodiments require about 8 pounds per square inch of positive pressure to convey the reagents through the tubing into the dispensing site within the incubation area. Due to the length of the tubing and the amount of positive pressure that must be applied, the reagent fluids sometimes release entrapped-air. The released air forms air pockets that block fluid flow in the tubing. This undesirable result is called "outgassing."

SUMMARY OF THE INVENTION

The invention provides more efficient systems for conducting multi-step analytical procedures that require the dispensing of fluids. The systems that embody the features of the invention significantly reduce the distance between the fluid source and the dispensing site. Yet, the systems do not also require a dedicated mechanism to manipulate the fluid dispensing nozzle. The systems work in a highly automated manner to maximize the throughput of the system, while also assuring accuracy and reproducible results.

The invention provides a system for processing a biologic specimen. The system includes a work station having a source of fluid that is to be added to the specimen during processing. The work station includes a fluid dispensing area and a nozzle for dispensing the fluid.

The system also includes a carrier mechanism. The carrier mechanism operates in a first mode for movement in the work station during fluid dispensing operations. The carrier mechanism also operates in a second mode for movement outside the work station to do another processing function not involving the work station. A controller mechanism selectively switches the mode of operation of the carrier mechanism between its first and second modes.

According to the invention, the system includes a docking mechanism that couples the nozzle to the carrier when it operates in its first mode to help dispense fluid. The docking mechanism releases the nozzle from the carrier when it operates in its second mode, freeing the carrier to do other processing functions out of association with the nozzle.

In a preferred arrangement, the work station includes a holder for the nozzle. The nozzle rests in the holder when fluid dispensing operations are not required. When the carrier mechanism enters its first operational mode, the docking mechanism attaches the nozzle to the carrier mechanism. The carrier mechanism moves the attached nozzle into and out of its holder. The carrier mechanism transports the attached nozzle to the fluid dispensing area of the work station. The docking mechanism also operates, when the carrier mechanism enters its second operational mode, to return the nozzle to its holder and to there release itself from the nozzle. This frees the carrier mechanism for movement outside the work station out of association with the nozzle.

In a preferred arrangement, the system washes the nozzle while it rests within the holder.

In a preferred arrangement, the system includes a second work station for performing a second processing function on the specimen. When operated in its second mode in this arrangement, the carrier mechanism works at the second work station free of association with the nozzle.

For example, the second work station can contain a mechanism for detecting the presence of a targeted material in the specimen, and the carrier mechanism can serve to transport the specimen to the detecting mechanism. Alternatively, the second 10 workstation can contain a mechanism for incubating the specimen, and the carrier mechanism transports the specimen to and from the incubating mechanism.

In this preferred arrangement, when operated in its first mode, the carrier mechanism also serves to transport the specimen to the fluid dispensing area and to manipulate the nozzle to align the nozzle with the specimen that is to receive the fluid. Still, when operated in its second mode, the carrier mechanism releases the nozzle to transport the specimen to the second work station free of association with the nozzle and its connected tubing.

According to the invention, a single carrier mechanism can be used to assist in multiple processing functions, including the dispensing of fluids. Still, the dispensing nozzle and all other fluid delivery components of the dispensing station can be located close together, even though the carrier mechanism itself can operate far away from the dispensing area. Because the carrier mechanism can release the nozzle after fluid dispensing operations, the lengths of tubing supplying fluid to the nozzle need not be long enough to permit transport of the nozzle away from the dispensing area, where the carrier mechanism serves other processing functions. Because the system requires only short lengths of the tubing, the amount of positive pressure required to convey fluid in the fluid dispensing area can be considerably reduced. This reduces the chance of forming air blocks caused by fluid outgassing.

Other features and advantages of the invention will become apparent upon considering the accompanying drawings, description, and claims.

BRIEF DESCRIPTION OF THE DRAWINGS

FIG. 6 is an enlarged perspective view of the carrier mechanism associated with the system, taken from left side, showing the movable platform that holds the specimen tray in its outward extended position;

FIG. 8 is a perspective view of the tray and associated cover that hold specimens during processing within the system;

FIGS. 11A, 11B, and 11C are perspective views of the movable platform operating within a holding station to remove a specimen tray, leaving the cover behind, as viewed from the inward facing side of the holding station;

FIGS. 15B-1 and 15B-2 together provide a schematic flow chart showing the sequence of calibrating the position of the platform relative to the optical channels at the photometric detecting station;

FIG. 18 is an enlarged exploded view of the reagent dispensing nozzle, its holder, and the associated docking fixture that embody the features of the invention;

FIG. 19 is an enlarged side section view of the reagent dispensing nozzle, its holder, and the associated docking fixture shown in FIG. 18, with the docking fixture being moved into engagement with the nozzle;

DESCRIPTION OF THE PREFERRED EMBODIMENTS

Figure 1:
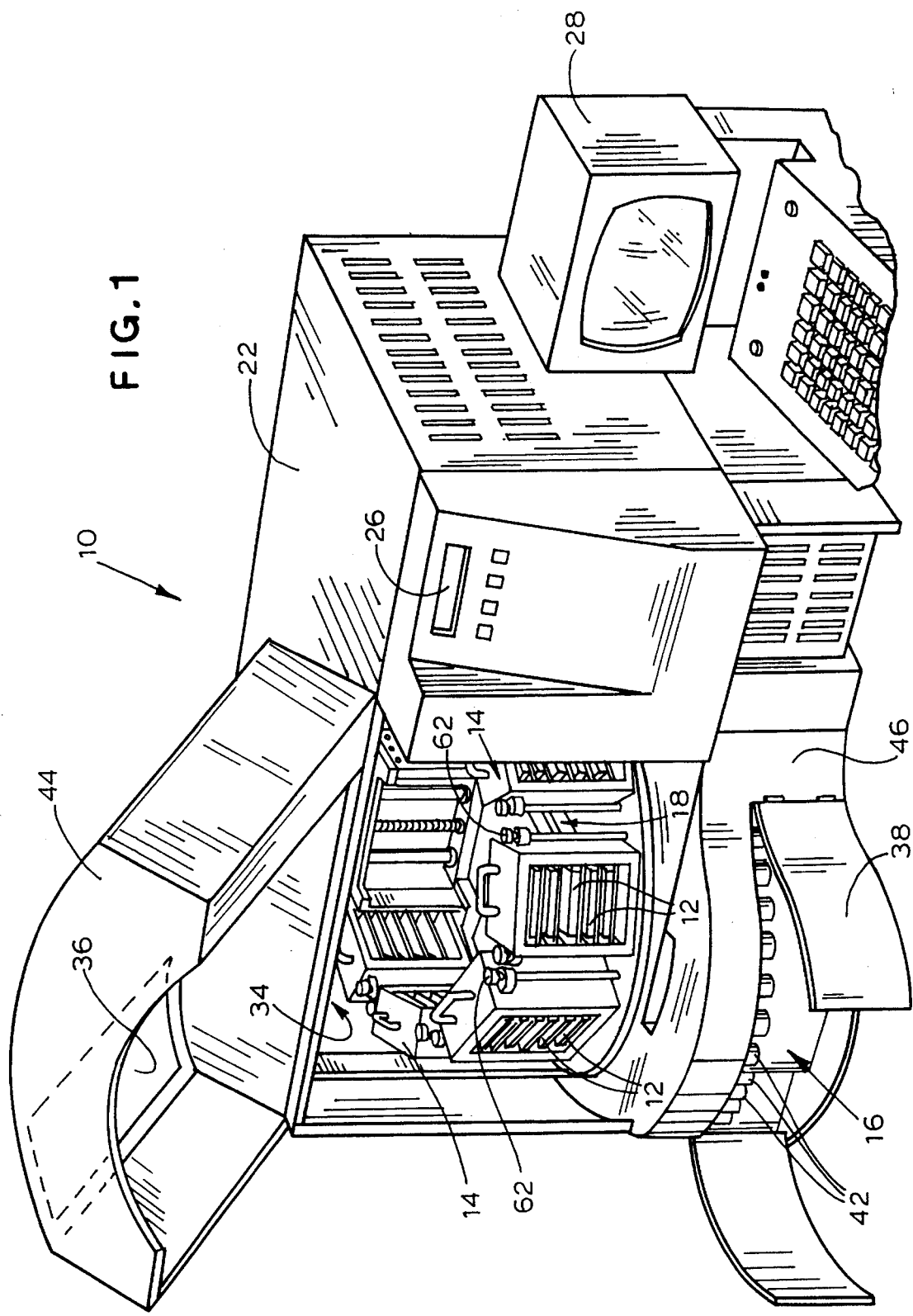
FIG. 1 is a perspective view of the front and right sides of a processing system that embodies the features of the invention, with some access panels and doors open to expose the interior portions to view.
Figure 2:
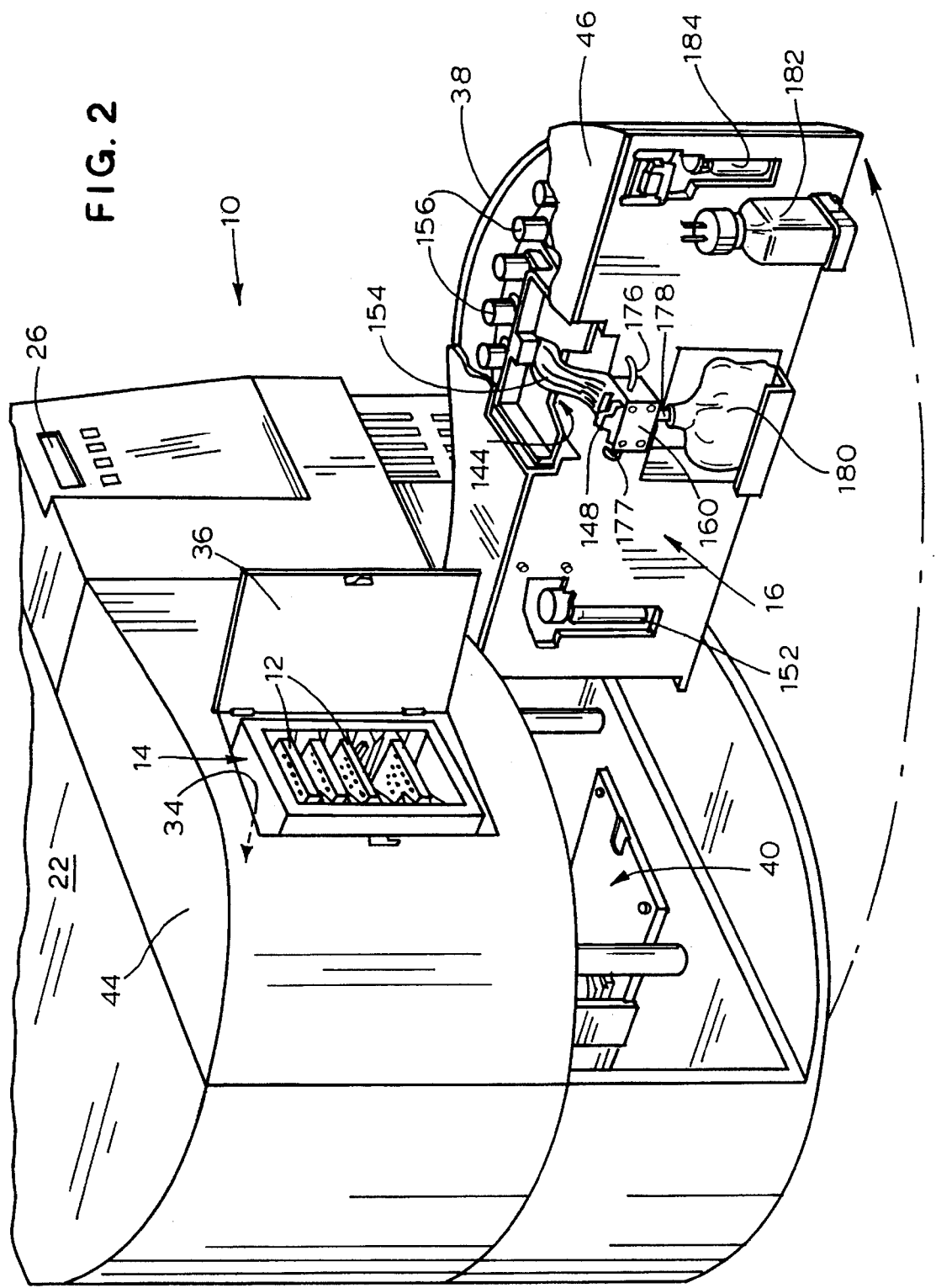
FIG. 2 is a perspective view of the front and left sides of the system shown in FIG. 1, with other access panels and doors open to expose the interior portions to view.
Figure 3:
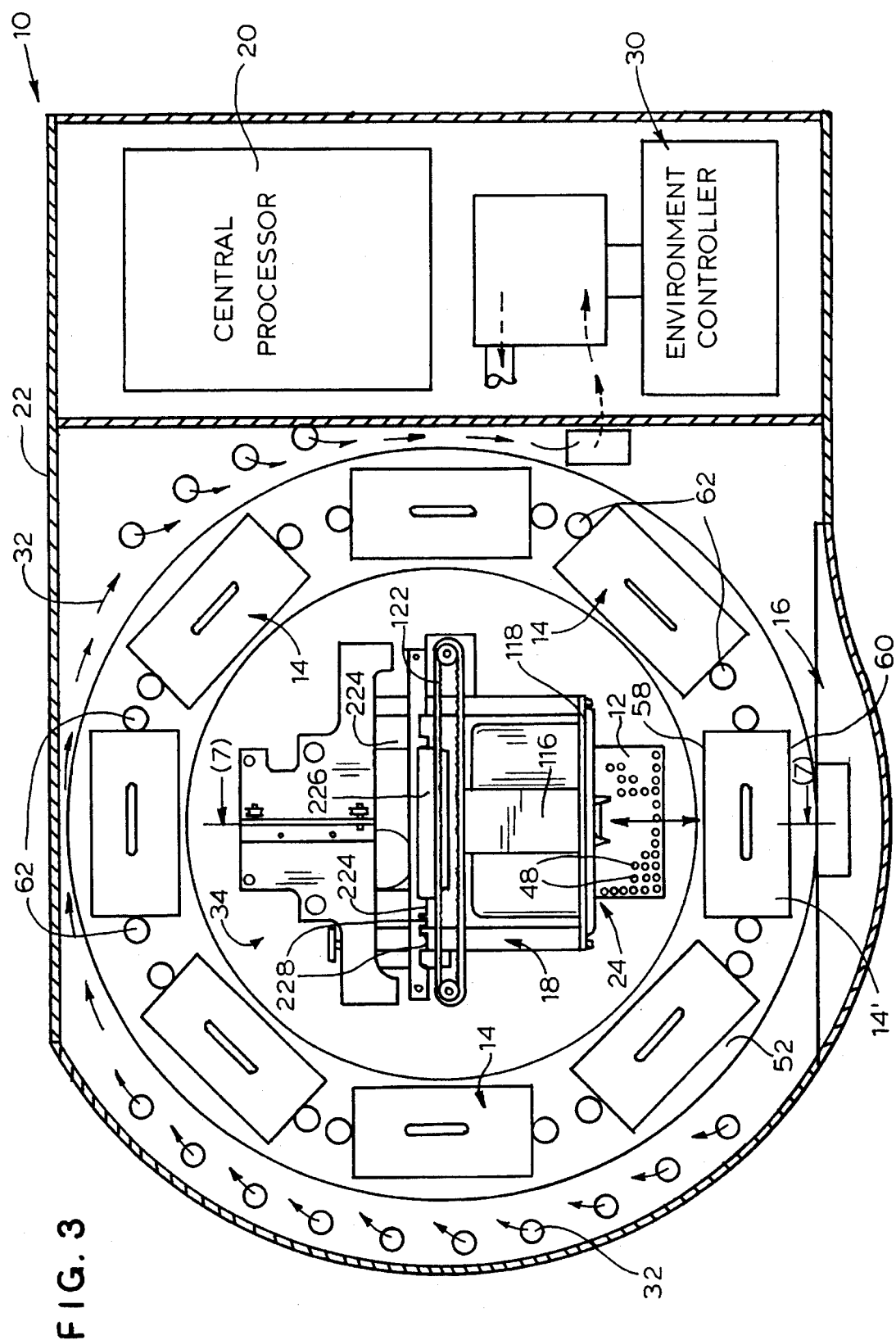
FIG. 3 is a top view of the interior of the system shown in FIG. 1, with some portions shown diagrammatically.

FIGS. 1 to 3 show the general arrangement of an analytical system 10 that incorporates the features of the invention. The analytical system 10 can be used in different environments to carry out different types of analytical, laboratory, and clinical procedures.

The invention can be used in association with systems that require accurate and reproducible transfers of fluid in clinical, medical, and industrial environments. The invention also can be used in association with systems that do assays for targeted materials or that analyze and identify biologic specimens.

This Specification describes a preferred embodiment of the invention operating as part of a device for screening liquid samples to identify microorganisms and test for their susceptibility to certain antibiotics.

In this use, the system 10 handles trays 12 carrying previously prepared suspensions of microbiologic specimens. The system 10 incubates the specimens within the trays 12, adds reagents to them, and analyzes them according to a prescribed protocol. The system 10 carries out these processes by sequentially transporting the specimen trays to various work stations 14, 16, 18 under the control of an onboard central microprocessor 20 (see FIG. 3). The central processor 20 is preprogrammed to follow at least one prescribed analytical protocol.

The nature and number of work stations in the system 10 can vary. In the illustrated embodiment, the system 10 includes stations 14 that hold the specimen trays 12 for incubation; a station 16 that dispenses reagents into the specimen trays; and a station 18 that detects and quantifies the growth of microorganisms in the specimen trays. As will be described in greater detail later, the detection station 18 measures microbic growth by either photometric or fluorometric techniques.

A cabinet 22 encloses the stations 14, 16, and 18 and the central processor 20. A carrier 24 10 transports the trays 1.2 among the stations 14, 16, and 18 within the cabinet 22 under the control of the central processor 20. The operator sends and receives system status and control information from the central processor 20 through an onboard input/output panel 26. A nearby input/output display cathode ray tube (CRT) and keyboard console 28 is also linked by cable to the central processor 20 (as FIG. 1 shows).

As FIG. 3 shows, the system 10 also includes an onboard environment controller 30 operated by the central processor 20. The controller 30 maintains a circulating air flow pattern 32 (shown by arrows in FIG. 3) through ducting within the principal processing region 34 of cabinet 22, where the holding stations 14 are located.

The air flow pattern 32 is heated and humidified to establish conditions necessary to incubate the specimens carried in the holding stations 14. The air flow pattern 32 typically maintains a temperature of about 37 degrees C. within the main incubation region 34.

The cabinet 22 includes doors 36 and 38 that permit periodic access into the enclosed interior regions of the cabinet 22.

The door 36 opens into the main incubation region 34 (see FIG. 2). When open, the door 36 allows the operator to load or remove specimen trays from a holding station 14. To preserve the incubating conditions within the region 34, the central processor 20 normally locks the door 36 to prevent unrestricted access. The central processor 20 opens the door 36 only in response to a proper access request code, which the operator enters using the console 28.

The door 38 opens into the lower region 40 of the cabinet 22, where the reagent dispensing station 16. When open, the door 38 allows the operator access to the interior of the reagent dispensing station 16 to load or remove reagent source containers 42. Since the interior of the reagent dispensing station 16 is largely isolated from the main incubation region 34, the operator can open the door 38 without first entering an access request code to the central processor 20.

Larger service panels 44 and 46 on the cabinet 22 can be opened to provide greater access for maintenance and repair when the system 10 is shut down. The service panel 44 opens into the main incubation region 34. The service panel 46 opens into the lower region 40 and carries the entire reagent dispensing station 16.

Figure 4:
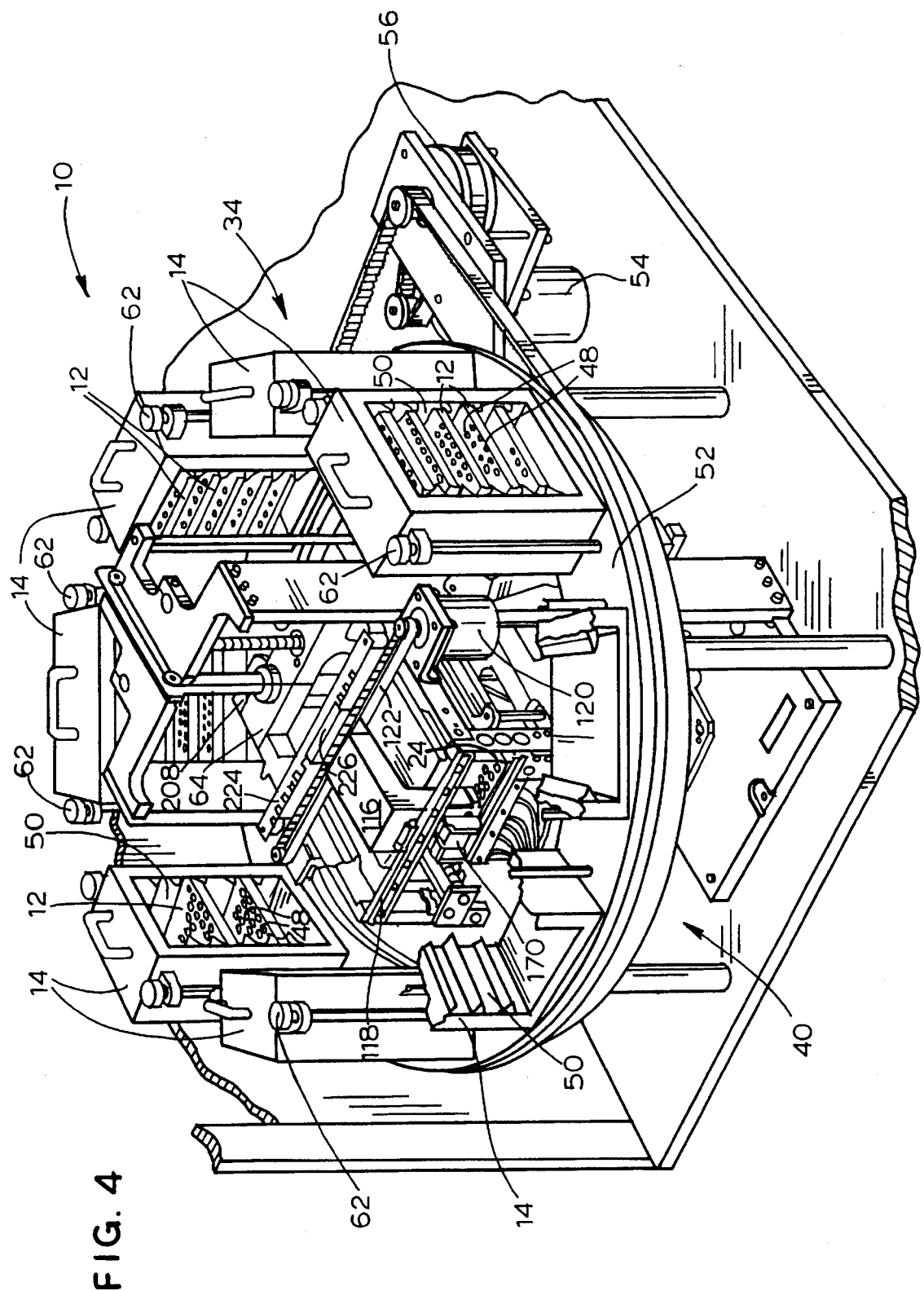
FIG. 4 is a perspective view of the interior regions of the system, showing the tray holding stations, the detecting station, and associated carrier mechanism, with portions broken away.

As FIG. 4 best shows, the holding stations 14 are vertically stacked into towers within the main incubation region 34. The number of holding stations 14 can vary, as can the number of trays 12 each holding station 14 carries. In the illustrated embodiment, there are eight holding stations 14, each containing six slots 50 to hold individual specimen trays 12 (see FIG. 9 also).

A carousel 52 moves the stacked holding stations 14 in a circular track around the carrier 24.

A first stepper motor 54 powers an associated belt drive 56 under the control of the central processor 20 to index the carousel 52. In this way, each holding station 14 can be brought to an access position, which holding station 14' occupies in FIG. 3. In this position, one side 58 of the holding station 14' faces inward toward the carrier 24, while the other side 60 faces outward toward the access door 36.

In the illustrated and preferred embodiment, a pair of tie-down bolts 62 attach each holding station 14 to the carousel 52. By unfastening the tie-down bolts 62, the operator can remove individual holding stations 14 for maintenance, cleaning, or sterilization.

Each tray 12 stacked within the holding station 14 includes an array of specimen wells or cuvettes 48 (as FIG. 8 best shows) arranged in aligned rows and columns. In the illustrated embodiment, each tray 14 includes ninety-six wells 48 arranged in eight rows of twelve wells 48 each.

The trays 12 are intended to be a single-use, disposable component of the system 10. So, the trays 12 are typically made of an inert plastic material. The plastic material can be light transmissive to permit analysis of the specimens by photometry. Alternatively, the plastic material can be opaque to permit analysis of the specimens by fluorometry.

The tray wells 48 contain various reaction agents. When incubated, the specimens react with these agents within the wells 48 to create differing distinctive patterns of color or turbidity changes, or fluorescence in the tray 12. Sometimes, a reagent must be added to trigger the needed reaction for analysis. By creating and then analyzing these patterns, the system 10 detects the presence of a given type of microorganism and its degree of susceptibility to various microbiotic agents.

In use, the operator prepares a culture medium containing a suspension of the microorganism to be analyzed. The operator introduces this suspension into the wells 48 of a specimen tray 12. The operator does this task at a specimen preparation station (not shown) outside the system cabinet 22.

In the illustrated and preferred procedure, the operator places a cover 86 on the tray 12 to minimize fluid loss by evaporation (see FIG. 8). As FIG. 8 shows, the cover includes a pair of projecting tabs 88 that extend horizontally beyond two sides of underlying tray 12.

To place a tray 12 and cover 86 within a slot 50 for processing, the operator enters the designated access request code. The processor 20 maintains an inventory of trays 12 within the holding stations 14 (as will be described later), and, with it, the processor 20 locates the position of empty holding slots 50. Upon request, the central processor 20 provides the operator with a listing of empty holding slots 50. The operator uses this listing to designate a holding station 14 via the data input panel 26 or console 28. The central processor 20 indexes the carousel 52 to place the user-designated holding station 14 in the access position (where FIGS. 3 and 7A/B show holding station 14' to be). The processor 20 then unlocks the door 36.

Figure 9:
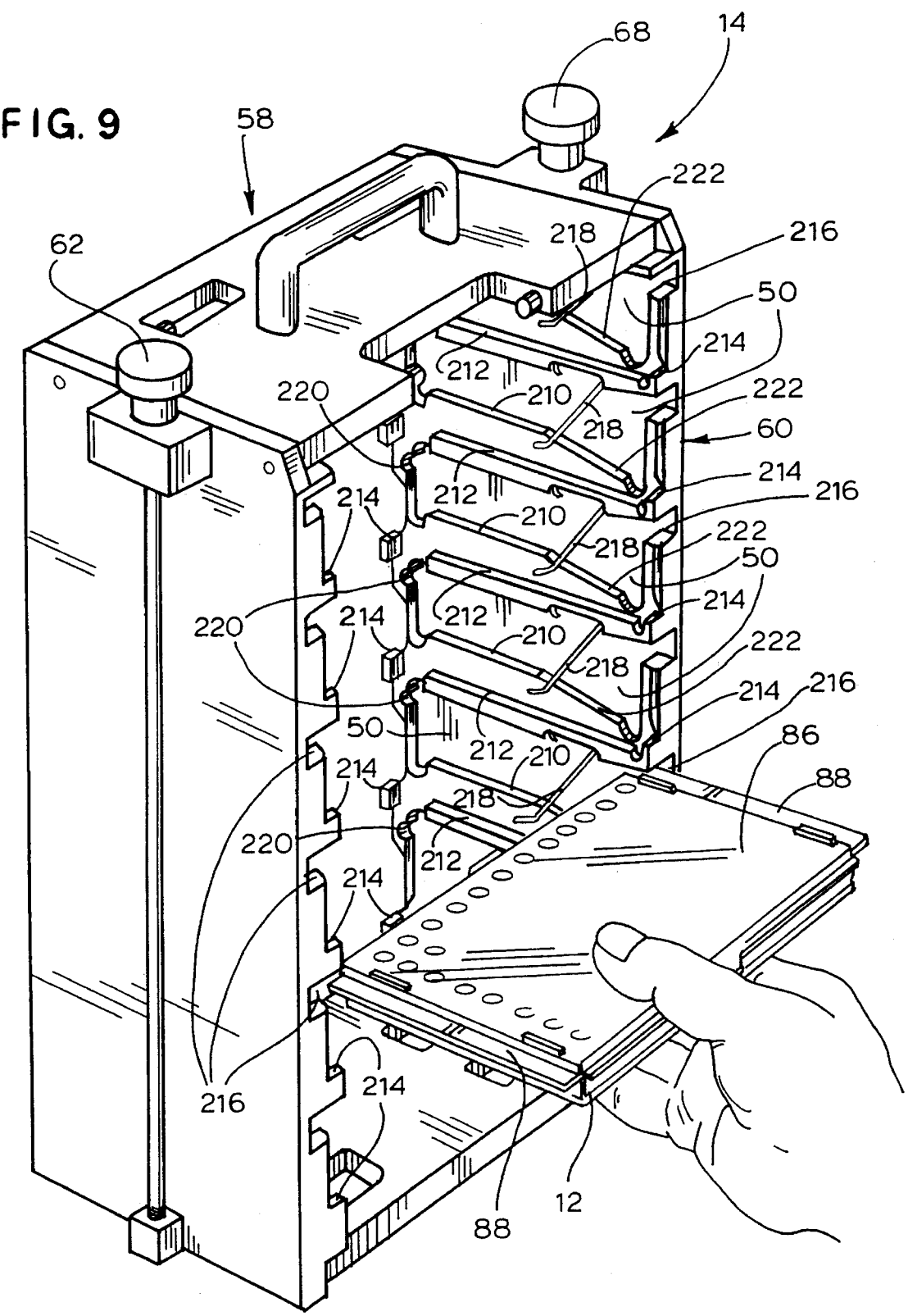
FIG. 9 is a perspective view of an operator loading a specimen tray (with cover) into the outward facing side of a holding station slot.

The operator manually loads the medium-filled specimen tray 12 with its cover 86 into an open holding slot 50 through the outward facing side 60 of the station 14 (as FIG. 9 best shows).

As FIG. 9 shows, the interior of each slot 50 is open except for opposite pairs of vertically spaced top and bottom support ledges 210 and 212. The bottom ledges 212 extend farther into the slot 50 than the top ledges 210. The bottom ledges 212' end with upturned edges 214 at both inward and outward facing sides 58 and 60 of the slot 50.

Figure 10:
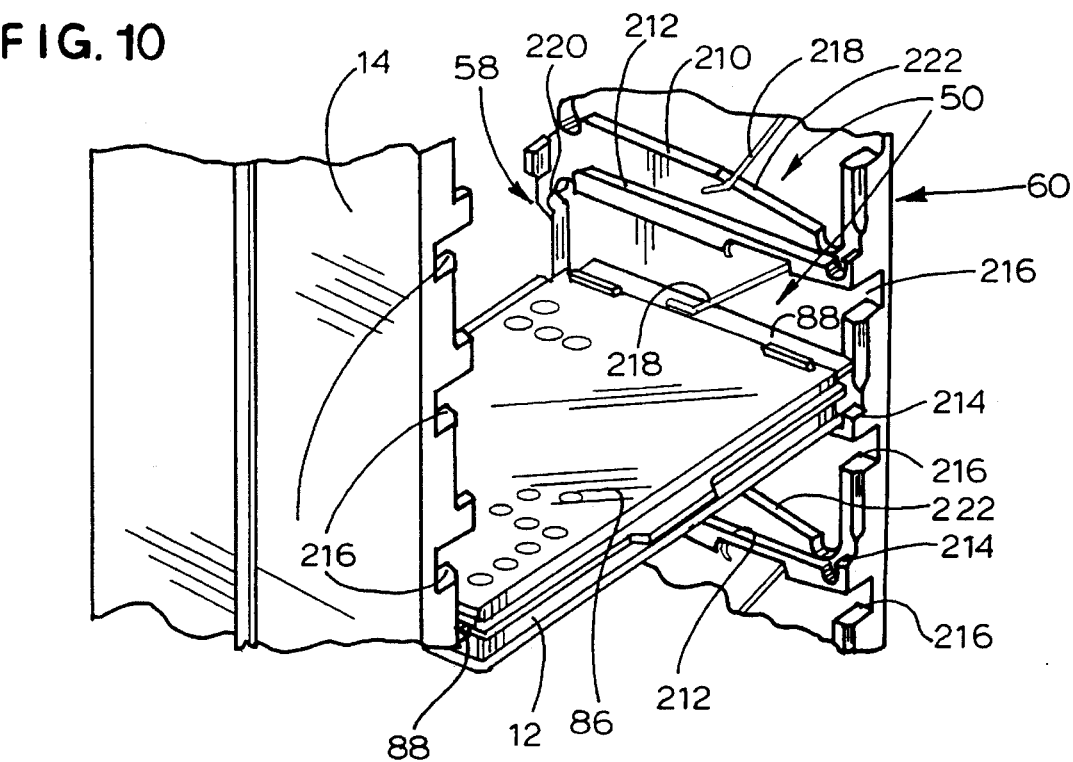
FIG. 10 is a perspective view of a specimen tray (with cover) stored within a holding station slot, as viewed from the outward facing side of the holding station.

As FIG. 9 shows, the operator inserts the tray 12 and cover 86 through a slotted opening 216 in the outward facing side 60 into the slot 50. As FIG. 10 shows, the bottom of the tray 12 comes to rest upon the bottom ledges 212. The upturned edges 214 prevent horizontal movement of the tray 12 within the slot 50. In the illustrated embodiment, when the tray 12 rests on the bottom ledges 212, the projecting tabs 88 on the overlying cover 86 extend above the plane of the top support ledges 210, making no contact with them. Springs 218 press against the projecting tabs 88 to hold the cover 86 on the underlying tray 12.

After loading the tray 12, the operator closes the door 36. From this point onward, the central processor 20 automatically conducts the analysis of the tray 12 without further involving the operator.

In carrying out its control operations, the central processor 20 sequentially actuates the carrier 24 to shuttle each tray 12 to and from the holding station 14, stopping either at the detection station 18 or the reagent dispensing station 16.

During a typical incubation period, the carrier 24 transports a given tray 12 several times between the holding station 14 and detection station 18 for successive analysis, with at least one intermediate stop at the reagent dispensing station 16.

The detection station 18 quantifies the microbic growth observed on each specimen tray 12'. The central processor 20 is linked to an external printer station (not shown). There, the processor 20 periodically generates written reports for the operator that contain a complete analysis for each specimen tray 12.

Figure 5:
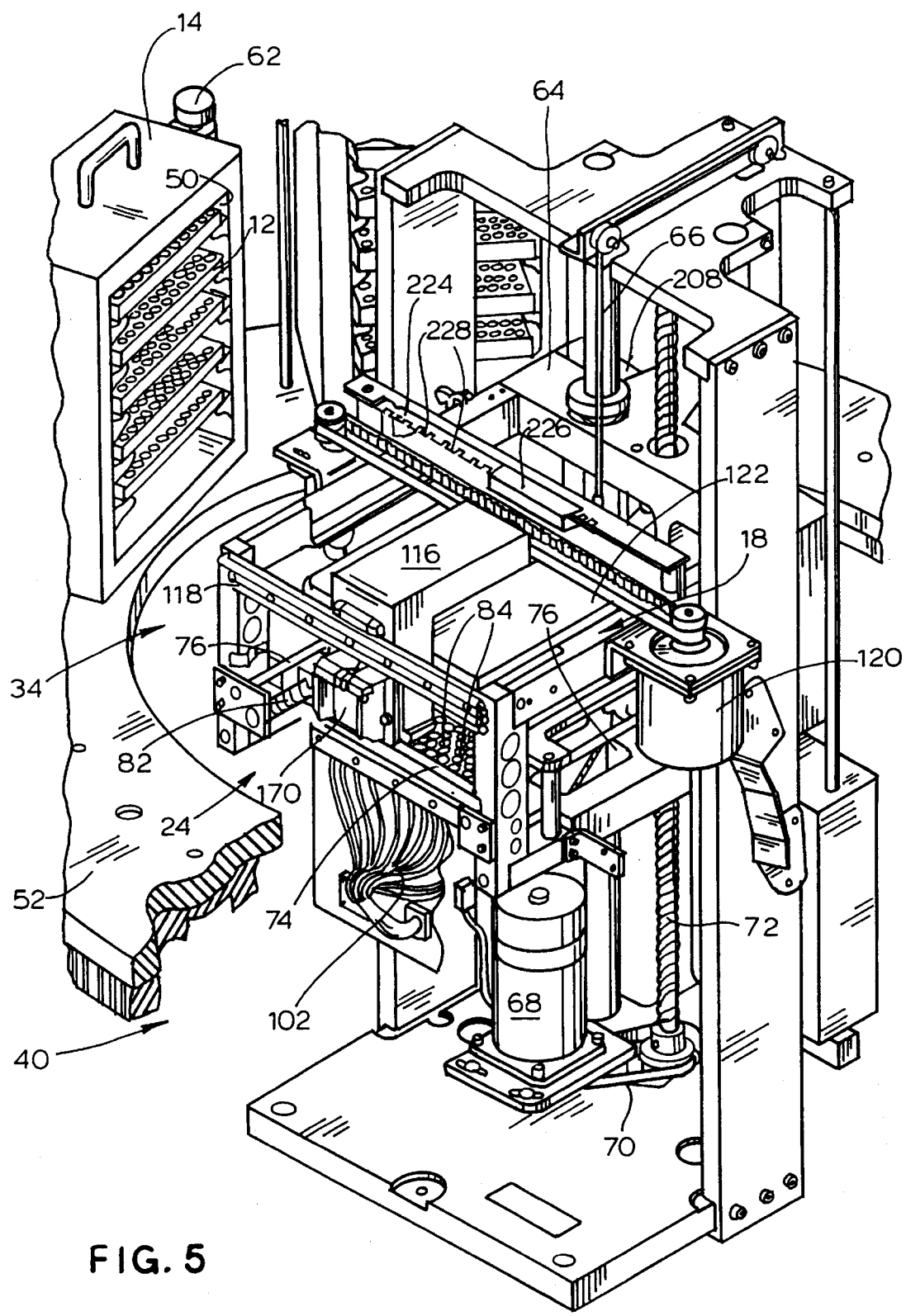
FIG. 5 is an enlarged perspective view of the right side of the interior regions of the system shown in FIG. 4.

FIGS. 5 and 6 show the details of the carrier 24. The carrier 24 includes a frame 64 supported on a pair of vertical shafts 66. A second stepper motor 68 powers an associated belt drive 70 to rotate a vertical axis lead screw 72 under the control of the central processor 20. The rotating vertical lead screw 72 moves the carrier frame 64 in a stepwise fashion up and down along the shafts 66. This mode of operation brings the carrier frame 64 into vertical alignment with any selected slot 50 of a holding station 14 occupying the access position.

The carrier 24 also includes a horizontal platform 74 mounted on a pair of tracks 76 on the frame 64. A third stepper motor 78 powers an associated belt drive 80 (see FIG. 6) to rotate a horizontal axis lead screw 82 under the control of the central processor 20.

Figure 7A:
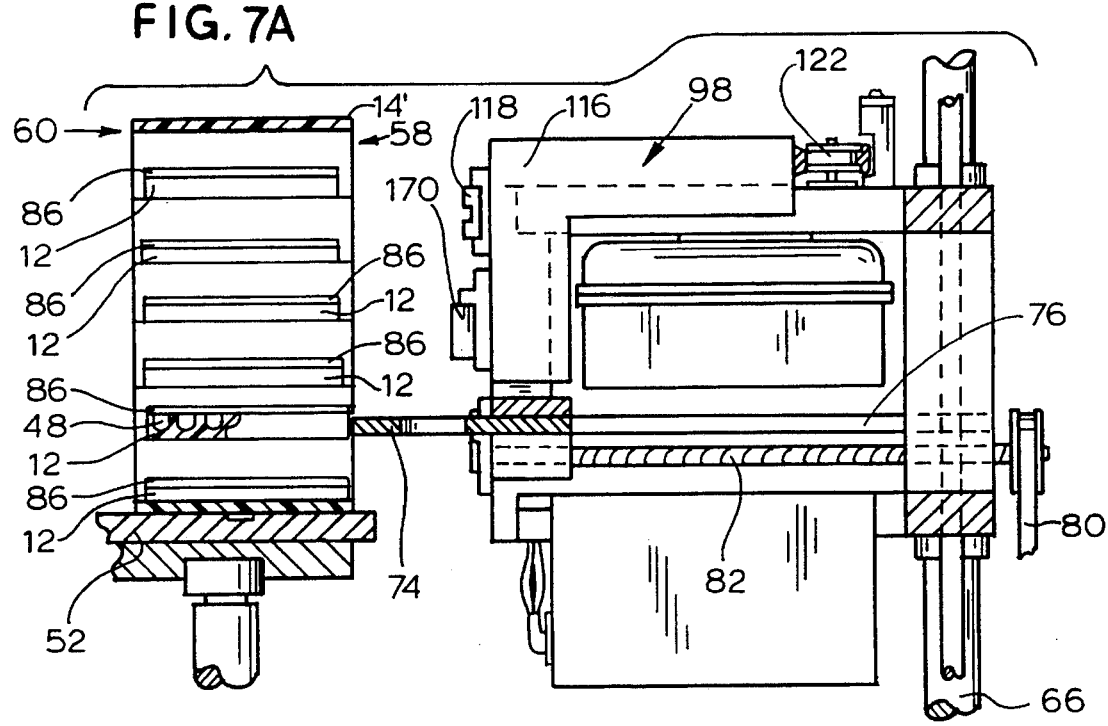
FIGS. 7A and 7B are side sectional views, taken generally along line 7—7 in FIG. 3, showing the movable platform picking up a specimen tray from a holding station.
Figure 7B:
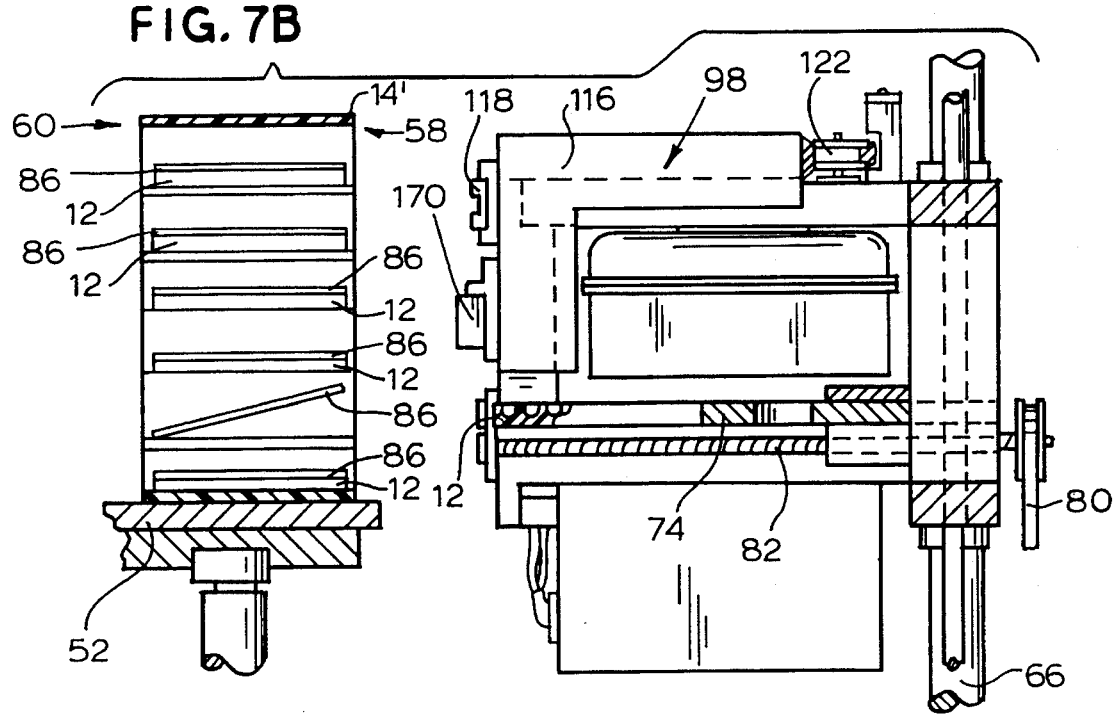

Rotation of the lead screw 82 advances the platform 74 in stepwise fashion along a horizontal path between a fully retracted position within the carrier frame 64 (see FIGS. 5 and 7B) and a fully extended position outside the carrier frame 64 (see FIGS. 6 and 7A).

As FIG. 7A shows, when moved toward its fully extended position, the horizontal platform 74 enters an aligned holding slot 50 beneath the occupying tray 12 through the inward facing side 58 of the station 14. Slight rotation of the vertical lead screw 72 lifts the platform 74. The open bottom of each slot 50 permits upward movement of the platform 74 into engagement with the underside of the tray 12.

Figure 14:
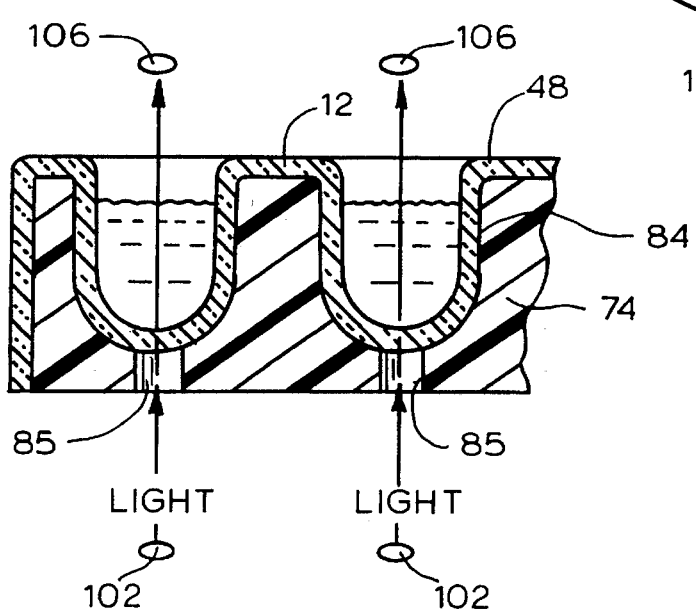
FIG. 14 is an enlarged side section view, taken generally along line 14—14 in FIG. 13, of the interior of two adjacent tray wells held upon the platform while in the photometric detecting station.

The platform 74 includes an array of pockets 84. The convex undersides of the tray wells 48 nest within the pockets 84 so that the tray 12 cannot slide horizontally on the platform 74. As FIG. 14 shows, the pocket bottoms define an opening 85 and do not interfere with the intended transmission of light through the tray wells 48.

Figure 11A:
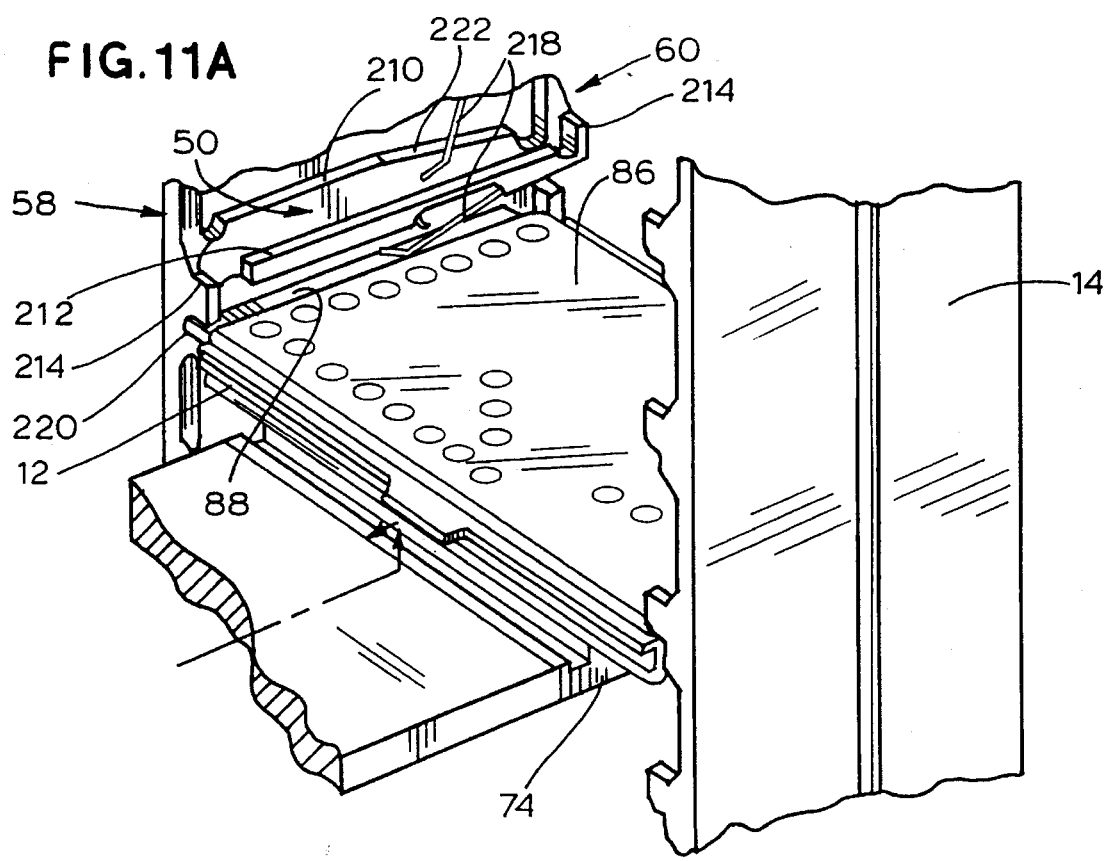

As FIGS. 11A shows, further operation of the lead screw 72 lifts the platform 74 and, with it, the covered tray 12 within the slot 50. The lifting movement (coupled with slight movement of the platform 74 inward, as shown by arrows in FIG. 11A) slips the inward facing edges of the projecting cover tabs 88 into upper detents 220, which are located within the slot 50 above the top support ledges 210.

As FIG. 11B shows, slight opposite rotation of the lead screw 72 lowers the tray 12, leaving the edges of the cover 86 engaged within the upper detents 220. As FIG. 11C shows, rotation of the horizontal lead screw 82 moves the platform 74 out of the holding slot 50. The platform 74 carries the engaged tray 12, but leaves the cover 86 behind (as FIG. 7B also shows).

As FIG. 9 best shows, the portion 222 of the top support ledge 210 that extends toward the outward facing side 60 of the slot 50 (i.e., the side the faces the access door 36) slopes downward toward the bottom support ledge 212. The springs 218 press against the cover 86 at the junction of the sloped portion 222 with the rest of the top support ledge 210.

As FIG. 11C shows, as the platform 74 withdraws the tray 12, the springs 218 pivot one end of the cover 86 down against the sloped portion 222, while the opposite end of the cover 86 remains engaged within the upper detents 220. The cover 86 assumes this tilted position within the slot 50 (as FIG. 7B also shows) as the platform 74 withdraws the tray 12. The cover 86 remains in this tilted position as the platform 74 transports the associated coverless tray 12 outside the holding slot 50.

Figure 12:
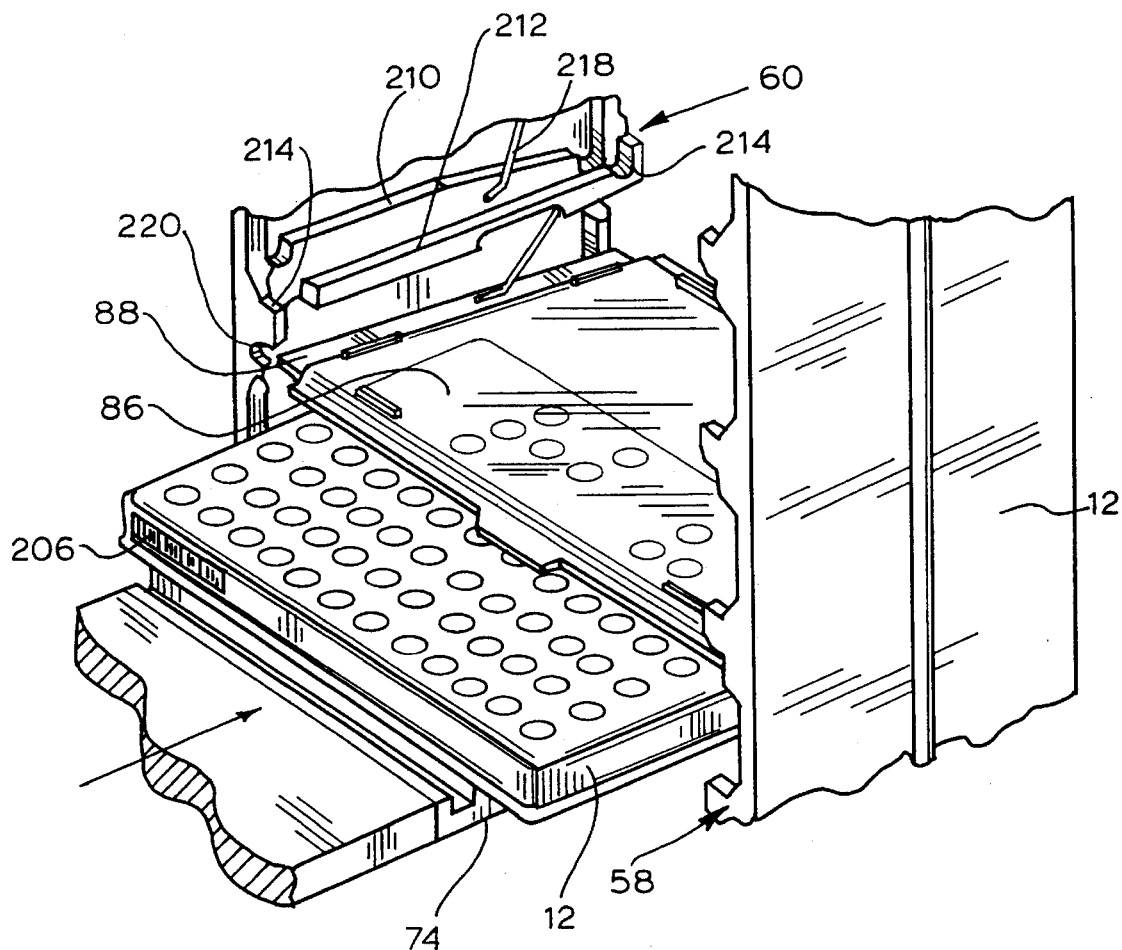
FIG. 12 is a perspective view of the movable platform operating within a holding station to insert a specimen tray, leaving the cover behind, as viewed from the inward facing side of the holding station.

As FIG. 12 shows, when the platform 74 returns the tray 12 to the slot 50, the entering edge of the tray 12 contacts the tilted portion the cover 86. The horizontal movement of the tray 12 pulls the cover 86 free of the detents 220, as FIG. 12 shows. The horizontal movement also pivots the cover 86 about the spring back into its original horizontal position on top of the tray 12. Slight rotation of the vertical lead screw 72 lowers the platform 64 from engagement with the now covered tray 12. Rotation of the horizontal lead screw 82 returns the platform 74 to its retracted position within the frame 64.

The central processor 20 maintains an inventory of the trays 12 undergoing processing within the System 10. As FIG. 8 shows, each tray 12 carries a unique identification label 206 written in bar code or another machine readable format. The carrier 24 includes a scanning device 208 (see FIG. 4) for reading the tray labels 206.

Each time the operator loads a new tray 12 into a holding station 14, the central processor 20 indexes the carousel 52 to bring the holding station 14 to a scanning position in alignment with the scanning device 208 (which is essentially 180 degrees from the access position previously described). The central processor 20 operates the vertical lead screw 72 to advance the scanning device 208 to view the label 206 of each tray 12 in the holding station 14, while operating the carousel 52 to advance the label 206 horizontally past the scanning device 208 to scan in the bar code information it contains.

In this way, the central processor 20 creates and updates an inventory record of trays 12 each time an operator loads a tray 12 into the system 10. The central processor 20 further updates the inventory record for each tray 12 to note the time and nature of the processing steps conducted. For each labeled tray 12, the inventory record establishes the holding station slot for the tray 12, the time the tray entered the system, the time and nature of each processing step involving the tray 12, and the results of the analyzes conducted on the tray 12.

The central processor 20 relies upon the preprogrammed protocol and real time inventory record it creates to control the processing sequence for each tray 12 within the system 10. The central processor 20 coordinates the rotation of the vertical lead screw 72 with the carousel belt drive 56 to orient the carrier 24 with a selected slot 50 of a holding station 14. Then, by operating the horizontal lead screw 82, the central processor 20 operates the platform 74 to remove the specimen tray 12 and later return the specimen tray 12 to the aligned holding slot 5a. The carrier 24 transports the engaged specimen tray 12 outside the holding slot 50 to either the detection station 18 or the reagent dispensing station 16, depending upon the commands of the central processor 20.

The operation of these two work stations 16 and 18 will now be described in greater detail.

In the illustrated embodiment, the carrier frame 64 supports the detection station 18. Still, it should be appreciated that the detection station 18 could be located away from the carrier frame 64 at another location within the cabinet 22.

Figure 13:
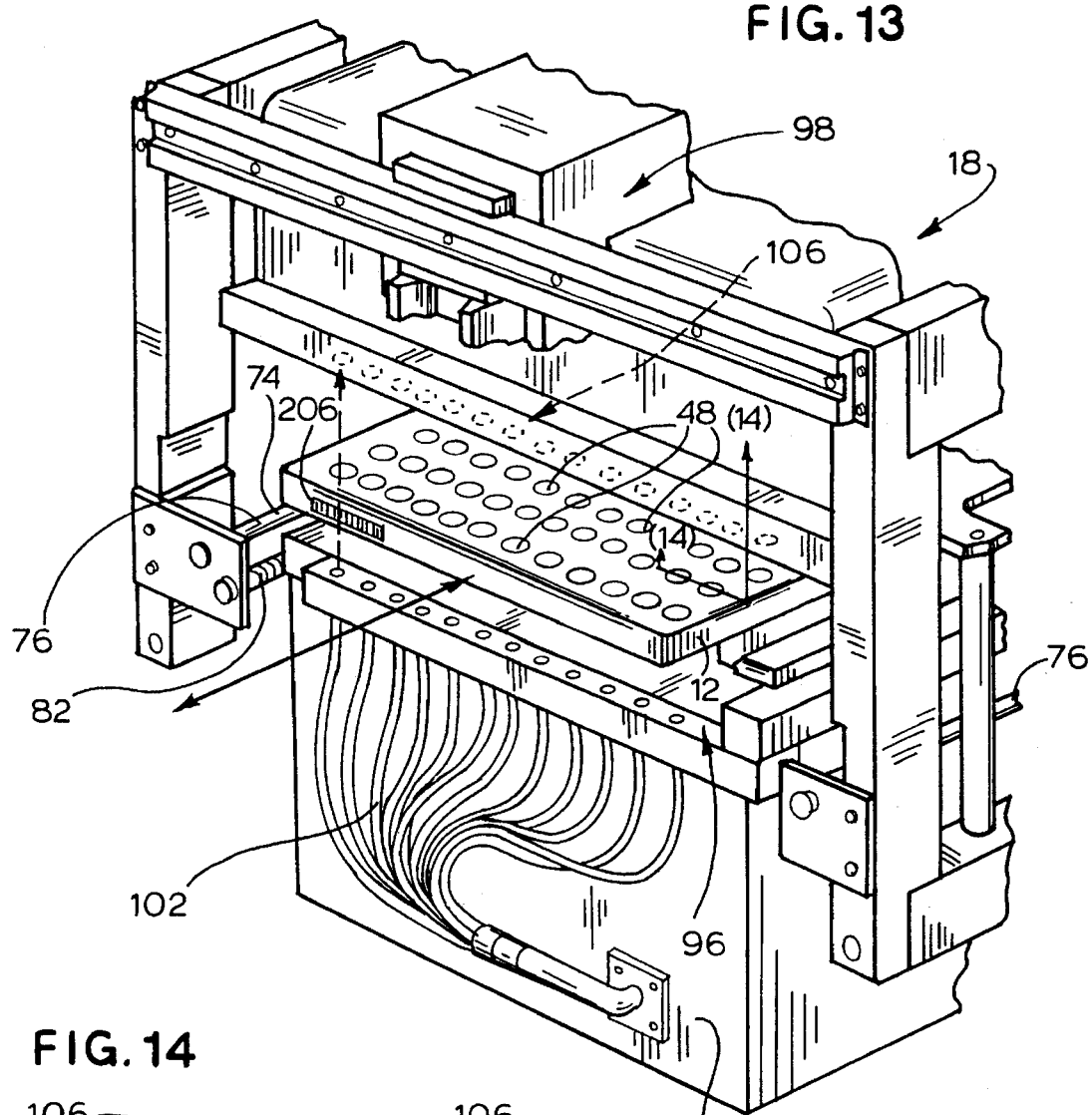
FIG. 13 is an enlarged perspective view of the photometric detecting station associated with the system shown in FIG. 1.

FIG. 13 shows the details of the detection station 18. As there shown, the detection station 18 includes both a photometric reader 96 and a fluorometric reader 98. The photometric reader 96 optically detects the presence of either color change or turbidity in a given specimen and by that derives a measure of microbiotic activity. The fluorometric reader 98 detects fluorescence within a given specimen to measure microbiotic activity. Whether a given specimen undergoes analysis by the photometric reader 96 or the fluorometric reader 98 depends upon the particular protocol of the analytical procedure that the central processor 20 follows.

Figure 15:
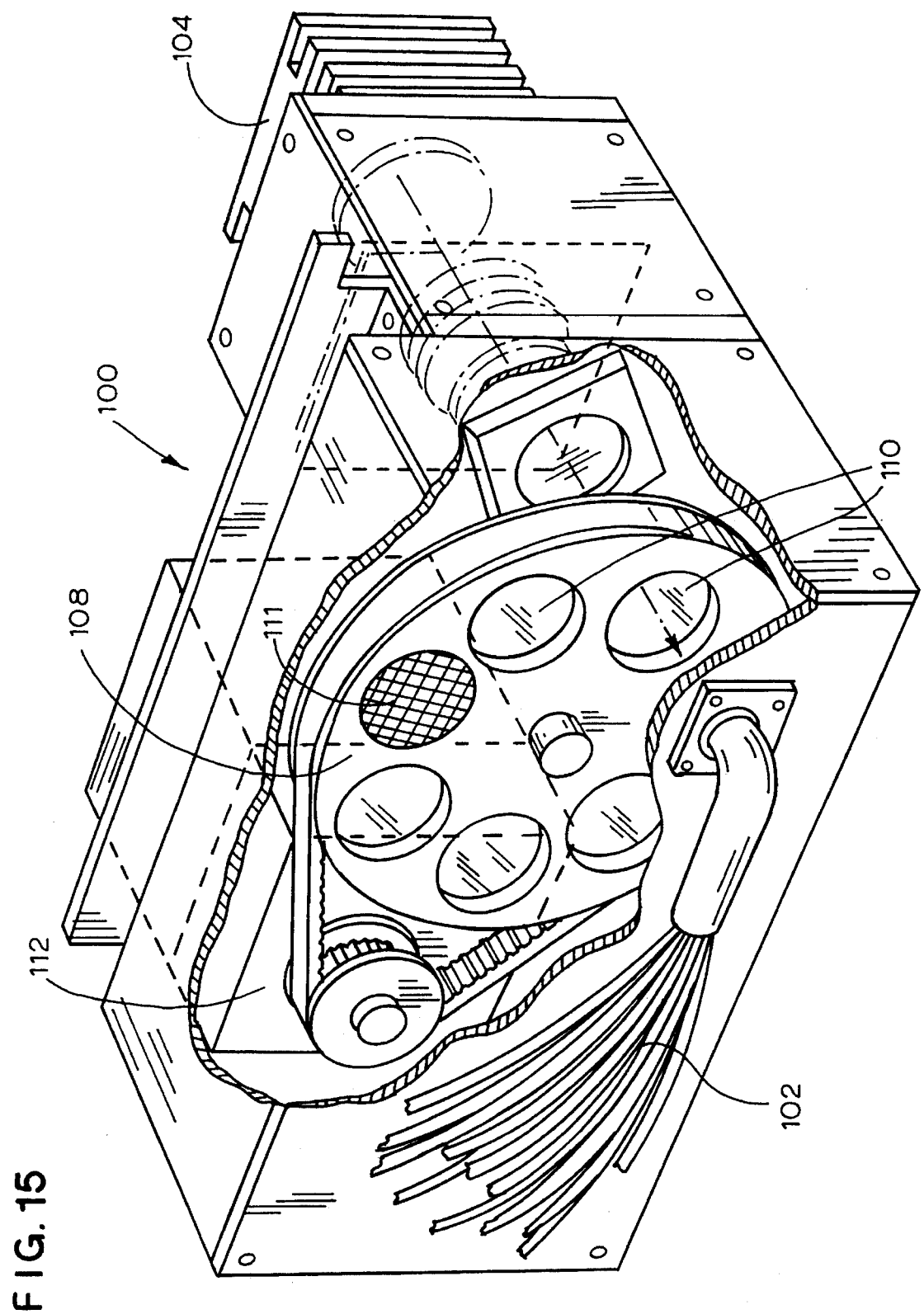
FIG. 15 is an enlarged perspective view, with portions broken away, of the light source associated with the photometric detecting station shown in FIG. 13.

The photometric reader 96 includes a light source assembly 100 comprising twelve fiber optic emitter lines 102 that lead from a single light source 104 (the details of which are shown in FIG. 15). The optic emitter lines 102 are arranged in a horizontal, spaced apart relationship on the frame 64 below the path of movement of the platform 74. The distance between adjacent optic emitter lines 102 corresponds with the distance between adjacent wells 48 within each row on the specimen tray 12.

In use (as FIGS. 13 and 14 show), the optic emitter lines 102 transmit light upward through the specimen tray 12 on the platform 74, individually illuminating one entire row (i.e., twelve wells 48) at a time. Each optic emitter line 102 includes a lens (not shown) that condenses the light beam exiting the optic fiber into a narrow vertical beam, by that maximizing the illumination of each well 48.

As FIG. 15 shows, the light source 104 is separated from the input end of each fiber optic line 102 by a color wheel 108. The wheel 108 includes six light filters 110 and one opaque disk 111 spaced about its periphery. Each filter 110 limits the light entering the fiber optic lines 102 to a discrete, predetermined wavelength. The opaque disk 111 blocks all transmission of light to the emitter line 102 when, for example, when the fluorometric reader 98 is in operation or during calibration, as set forth in more detail later. A fourth stepper motor 112 rotates the color wheel 108 to position the desired filter 110 or disk 111 in the light path under the control of the central processor 20.

As FIG. 13 shows, the photometric reader 96 also includes twelve photodiode detectors 106 paired with the twelve optic emitter lines 102. The twelve photodiode detectors 106 face the optic emitter lines 102 on the frame 64 above the path of movement of the platform 74. The photodiode detectors 106 sense light after its transmission through the specimens in the wells 48.

With the desired filter 110 positioned in the light path, the central processor 20 indexes the tray-carrying platform 74 stepwise between the twelve paired emitters and detectors 102/106. The photometric reader 96 includes a programmable gain amplifier 113 (see FIG. 15A) that is capable of providing fixed levels of amplification, called gain stages. A digital processor 114 analyzes the sensed signal at a preselected selected gain stage to determine either the color or turbidity of the specimens.

In use, multiple photometric readings are typically taken of the specimens at predetermined intervals during the incubation period.

Each emitter/detector pair 102/106 constitutes one independent optical channel C1 to C12 that, in use, transits one tray well 48. The central processor 20 independently calibrates each optical channel C1 to C12 to obtain a reading representative of the absorption of the sample within the associated tray well 48. Independent calibration allows the differences between the twelve individual channels C1 to C12 to be cancelled out. Independent calibration accommodates greater mechanical and electrical tolerances among the channels C1 to C12 than the calibration of all channels to a common reference point. Independent calibration cancels out these differences among the channels without adversely affecting the overall accuracy of the photometric reader 96.

The calibration procedure for each optical channel C1 to C12 is the same. The procedure begins with the platform 74 carrying no tray 12. The central processor 20 places the opaque disk 111 in the light path to block transmission of light to all optical channels. A separate reading is taken for each channel at each gain stage of the amplifier 113. These readings represents the dark signals (electrical offset) for each gain stage of each channel. The central processor 20 retains these readings for each optical channel in memory.

The central processor 20 then sequentially brings a filter 110 into the light path. While no tray 12 occupies the platform 74, a reading is taken. The central processor 20 selects the gain stage of the amplifier 113 that achieves an on-scale reading. This becomes the preselected gain stage for that channel for that particular filter 110 (wavelength). The on-scale reading at that gain stage becomes the reference for that channel for that particular filter 110 (wavelength). Because each channel is calibrated independent of the other channels, each optical channel may and probably will have a different gain stage and reference for each filter 110.

The calibration procedure repeats this sequence for each filter (wavelength) 110, obtaining an associated gain stage and reference for each channel. The central processor retains these values in memory.

The central processor 20 thus maintains for each filter (wavelength) 110 three calibration values for each optical channel C1 to C12. These calibration values represent the gain stage (G) selected to obtain an on-scale reading for the filter 110; the reference reading taken at the selected gain stage ($R_G$); and the dark reading earlier obtained for the selected gain stage ($D_G$).

Figure 15A:
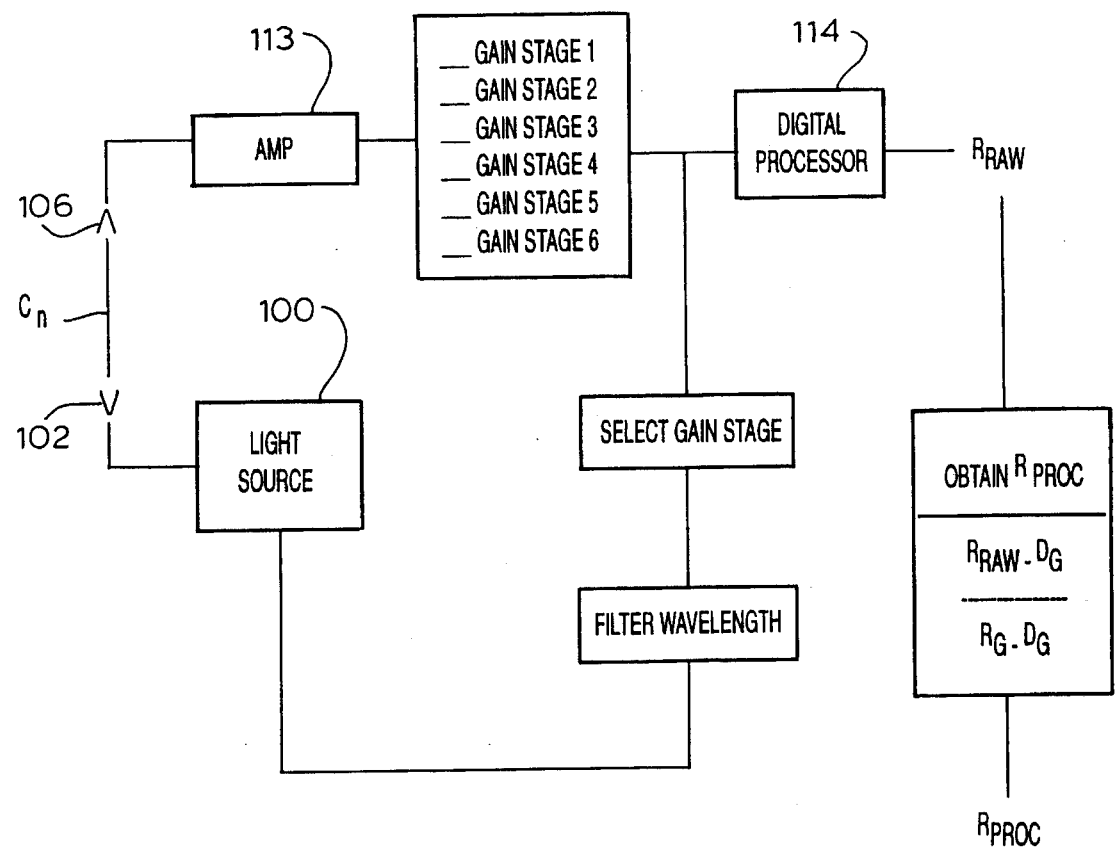
FIG. 15A is a schematic showing the sequence of obtaining a processing reading at the photometric detecting station.

As FIG. 15A shows with respect to each optical channel (designated $C_a$ in FIG. 15A), a subsequent reading in that optical channel at a particular filter wavelength ($R_{RAW}$) is taken at the selected gain stage (G) for that filter 110. The central processor alters the subsequent reading ($R_{RAW}$) to obtain a processing reading ($R_{PROC}$) for each optical channel, as follows:

$$R_{PROC} = \frac{(R_{RAW} - D_G)}{(R_G - D_G)}$$

The processing reading $R_{PROC}$ is representative of the absorbance of the sample taken at that optical channel. Due to the calibration process, the processing reading $R_{PROC}$ for each optical channel is hardware independent.

Figure 15B:
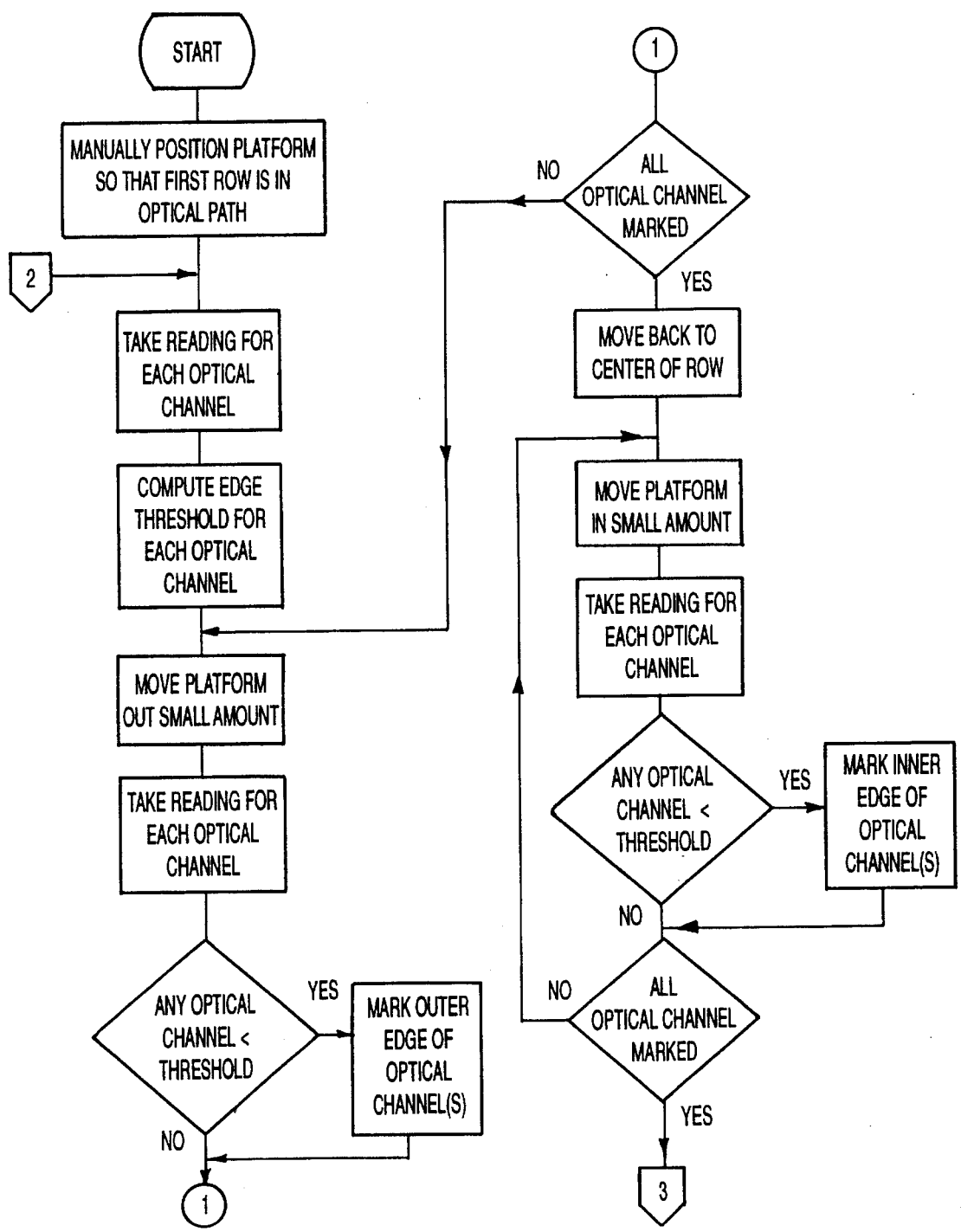
Figure 15C:
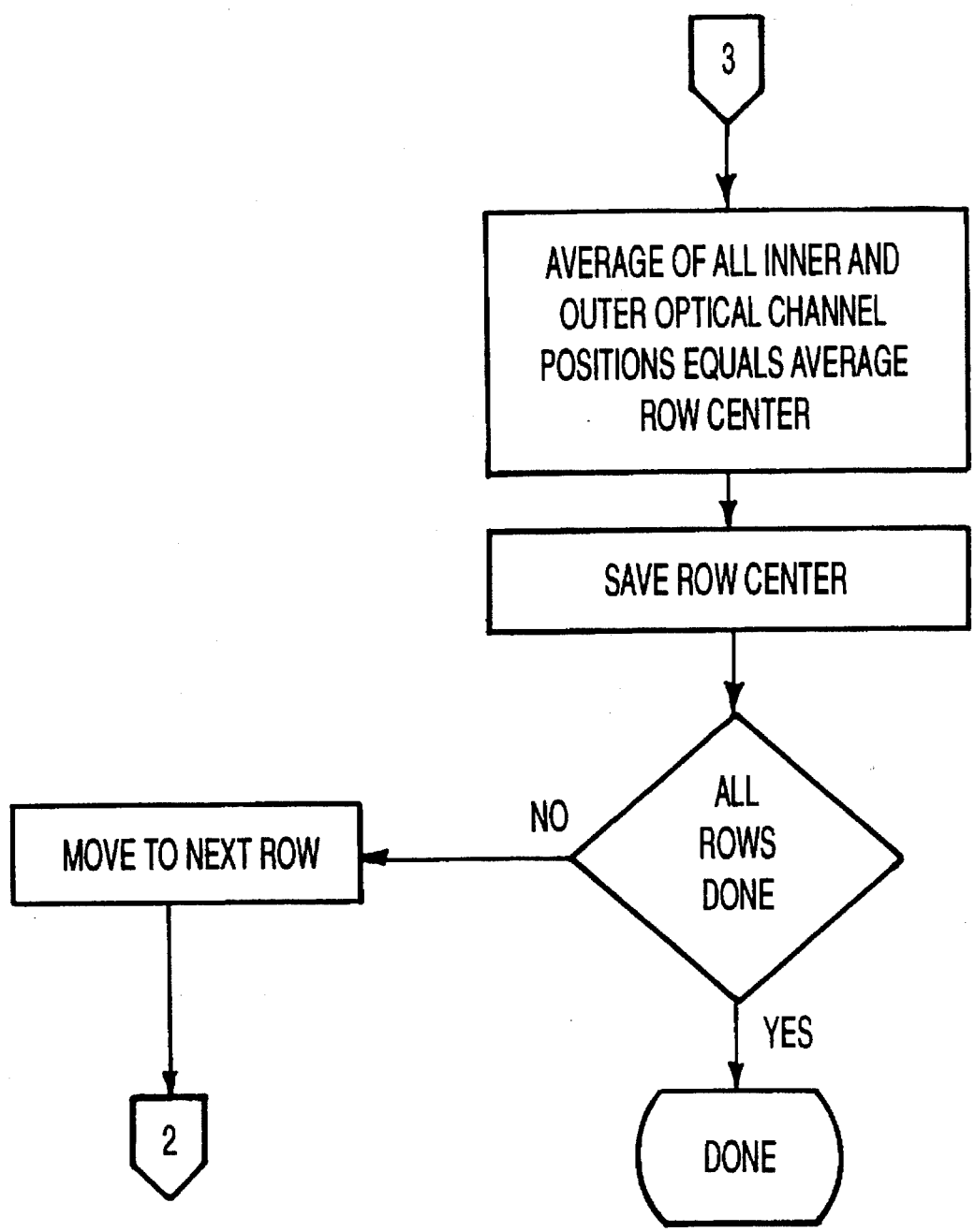

The central processor 20 also calibrates the position of the platform 74 relative to the optical channels to properly locate the openings 85 in the platform 74 within the light paths. FIG. 15B shows the sequence of the platform calibration procedure.

The platform 74 is drawn through the light paths. For each optical channel, the amount of light reaching the associated detector 106 increases as the outer edge of the associated opening 85 enters the light path. The light signal reaches a maximum value when the center of the opening 85 occupies the light path. The light signal then decreases as the inner edge of the opening 85 enters the light path to block the light.

As FIG. 15B shows, for each optical channel, the central processor 20 marks the position of the platform 74 (based upon the particular step of the stepper motor 78) when a preselected threshold value is reached at the inner and outer edges of the associated opening 85. The center of the opening 85 is determined for that particular optical channel by averaging these two marked positions. The determined centers for the optical channel are themselves averaged to derive an average center position for the stepper motor 78 for each row of openings 85.

Using the just described calibration procedure, the central processor 20 indexes the platform 74 to best position the centers of the openings 85 along each row into the optical channels. The openings 85 are fixed on the platform 74, and the tray is preformed so that the centers of its wells 48 nest within the platform 74 in registration with the centers of the openings 85.

The use of a precisely calibrated movable platform 74 in combination with a specimen tray 12 that precisely nests upon the platform 74, allows the central processor 20 to accurately equate the position of the platform 74 to that of each specimen tray 12 traversing the photometric reader 96.

Due to the prearranged, fixed relationship between the platform 74 and the tray 12, the calibration procedure just described and as set forth in FIG. 15B need be performed for each system 10 only upon initial setup and after repair and/or replacement of the platform 74 or its associated drive assemblies.

Figure 16:
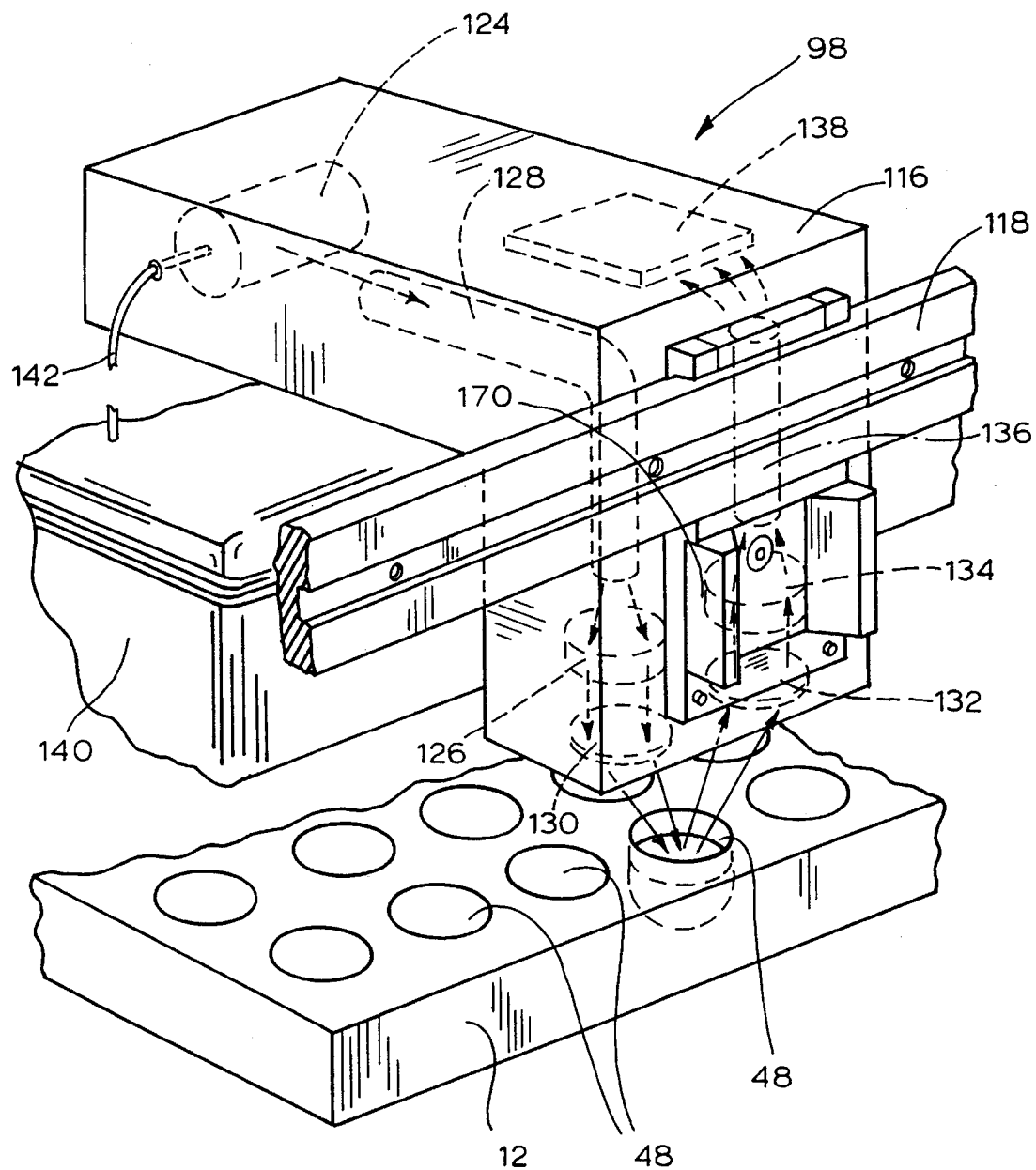
FIG. 16 is an enlarged perspective view of the fluorometric detecting station associated with the system shown in FIG. 1, with interior portions shown diagrammatically.
Figure 17:
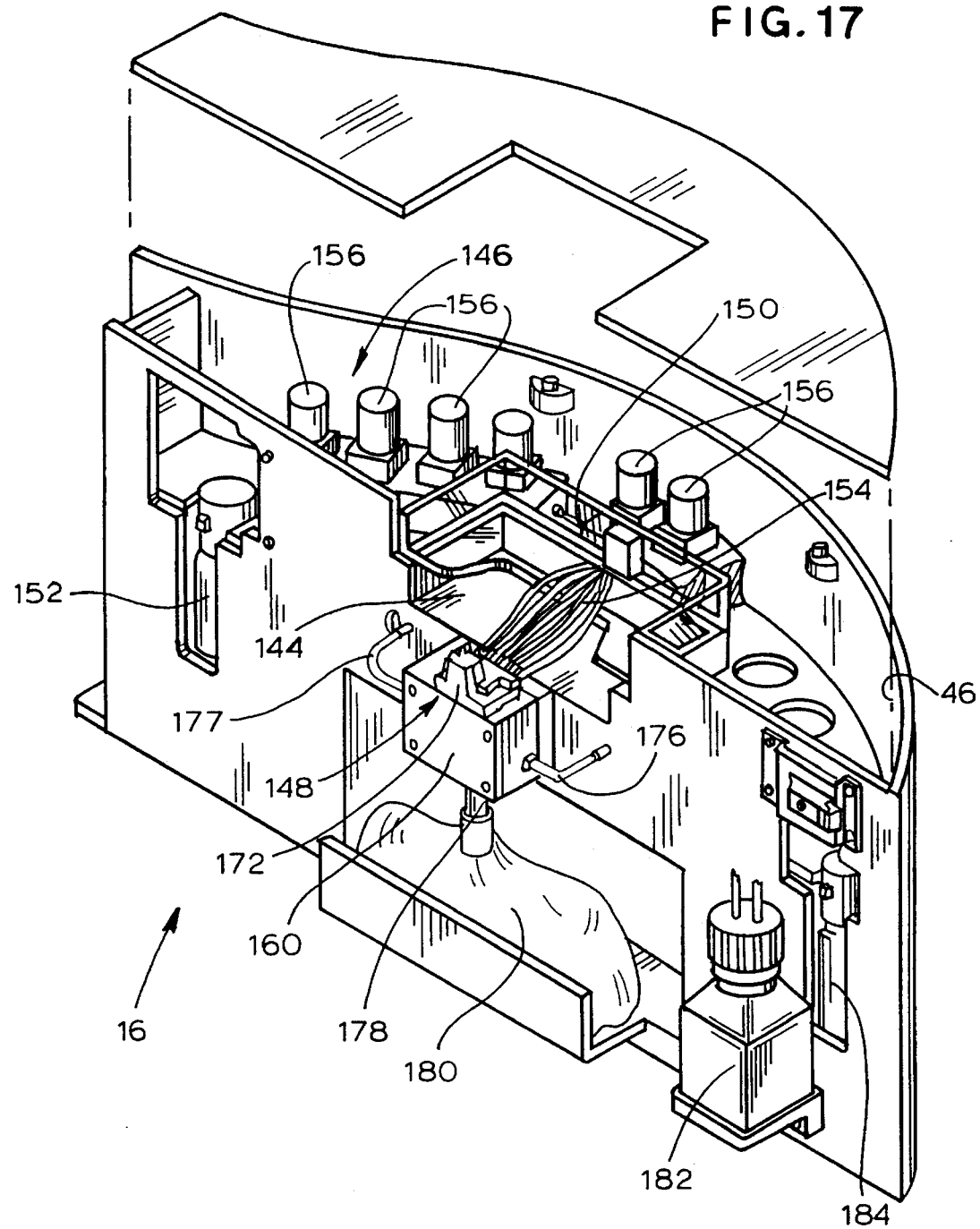
FIG. 17 is an enlarged perspective view, partially exploded, showing the rear portion of the reagent dispensing station carried within an access panel of the system shown in FIG. 1.

FIG. 16 shows the details of the fluorometric reader 98. The fluorometric reader 98 includes a movable head 116 that travels along a horizontal track 118 on the carrier frame 64 above the path movement of the platform 74. The track 118 extends transversely across the path of platform movement. A fifth stepper motor 120 (see FIGS. 4 and 5) powers an associated belt drive 122 that moves the head 116 back and forth along the track 118.

The head 116 encloses a fluorometer, the interior details of which are shown in FIG. 16. The fluorometer includes a source lamp 124 that directs light to an excitation filter 126 through a quartz light path 128. An output lens 130 directs the out coming light onto the specimen contained in an underlying well 48. The specimen contains a material that, in the presence of a target microorganism, reacts to the light energy by fluorescing.

The resulting fluorescence is directed by an input lens 132 to an emission filter 134 for the expected wavelength. A photomultiplier tube 136 and a preamplifier 138 translate the light signal to an analog output that is directly proportional to the amount of fluorescence detected.

An analog-to-digital converter 140 (which is carried on the frame 64 and is attached to the movable head 116 by a cable 142) converts the analog output of the photomultiplier tube 136 to digital output. The converter 140 also includes the power supply for components carried within the movable head 116.

In use, the carrier platform 74 indexes a row of wells 48 into position below the head 116. The central processor 20 moves the head 116 down the wells 48, obtaining the fluoresced light signal for each well 48 and transmitting it to the processor 140.

FIGS. 17 to 22 show the details of the reagent dispensing station 16. As previously stated, the reagent dispensing station 16 occupies the region 40 below the carousel 52 at the front of the cabinet 22 (see FIGS. 1 and 2). It is housed within the service panel 46 essentially out of the main incubation region 34 area of the system 10. The panel 46 contains a reagent dispensing area 144, a pressurized reagent source 146, and a reagent dispensing nozzle 148.

The source 146 contains different reagent types contained in individual containers or vials 42 (see FIGS. 1 and 15). Tubing manifold 150 connects each vial 42 to a positive pressure pump 152. Each reagent vial 42 also includes an outlet tube 154 with an inline solenoid valve 156 that is under the control of the central processor 20. When closed, the solenoid valve 156 blocks the flow of reagent from the pressurized vial 42. When opened, the solenoid valve 156 permits reagent to flow under positive pressure from the vial 42 through the associated outlet tubing 154.

The outlet tubing 154 for the reagent vials 42 all leads to the dispensing nozzle 148. The dispensing nozzle 148 includes individual fluid dispensing ports 158 (see FIG. 18), one for each type of reagent.

When the solenoid valve 156 opens for a particular source reagent vial 42, the particular reagent in the vial 42 flows under positive pressure out the associated dispensing port 158 in the nozzle 148. The dispensing ports 158 are symmetrically arranged at predetermined intervals relative to the centerline of the nozzle 148 to allow precise positioning over the intended well 48 by the stepper motors controlled by the central processor 20 (as will be described in greater detail later).

When not in use, a holder 160 retains the nozzle 148 on the dispensing station 16 away from the fluid dispensing area 144. In the illustrated embodiment, the holder 160 is located a short distance below the dispensing area 144 and close to the reagent source 146.

A movable latch 162 (see FIG. 18) within the holder 160 is biased by springs 164 into engagement with a tab 166 on the nozzle 148. This engagement locks the nozzle 148 in place inside the holder 160 (as FIG. 19 shows).

Tubing 176 periodically brings washing fluid from a source container 182 into the holder 160 using the positive pressure pump 184. The periodic pressurized spray of fluid washes the interior of the holder 160. It can also be used to wash the nozzle 148 resting within the holder 160. The washing fluid drains through an exit tube 178 into a disposable collection bag 180. Tubing 177 periodically brings pressurized air into the holder 160 to air dry the nozzle 148 after washing.

The compact arrangement of all components of the reagent dispensing station 16 out of the main incubation region 34 allows the reagent source 146 to be positioned close to the dispensing nozzle 148. The lengths of outlet tubing 154 supplying reagent to the nozzle 148 can be significantly shortened. The tubing 154 need be long enough only to allow the nozzle 148 to reach the holder 160 and the reagent dispensing area 144. The tubing 154 need not be long enough to allow the nozzle to reach beyond the reagent dispensing station 16 and into the main incubation region 34 of the system 10. Because of the short length of the tubing 154, the amount of positive pressure required to convey the reagent in the system 10 can be considerably reduced.

For example, compared with conventional arrangements, the reagent dispensing station uses only about 25% as much tubing. It also operates at a fluid pressure of only 3 PSI (pounds per square inch) instead of the 8 PSI that conventional systems must use. The reduction of positive pressure within the system considerably reduces the formation of air blocks caused by fluid outgassing within the tubing 154.

Figure 20:
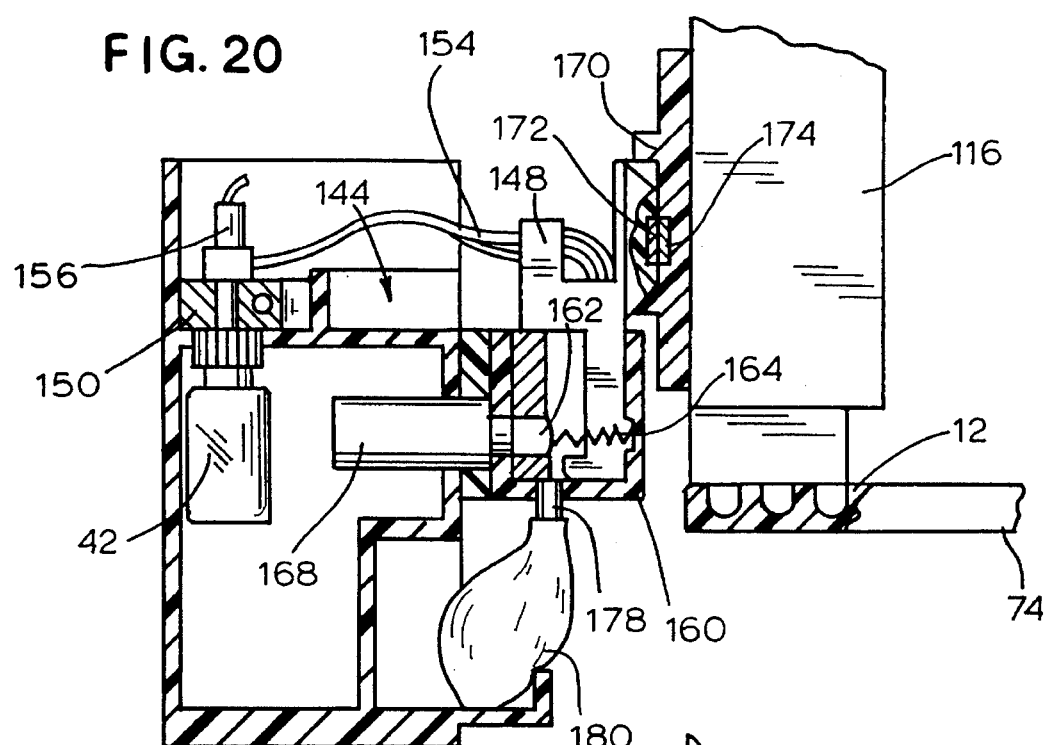
FIG. 20 is an enlarged side section view of the reagent dispensing nozzle, its holder, and the associated docking fixture shown in FIG. 18, with the docking fixture engaged with the nozzle.

A solenoid 168 selectively energized by the central processor 20 moves the latch 162 away from the nozzle tab 166 against the force of the biasing spring 164 (as FIG. 20 shows). This frees the nozzle 148 for removal from the holder 160 when it is time to dispense reagent.

The carrier 24 includes a docking fixture 170 for engaging the nozzle 148 to transport it between the holder 160 and the reagent dispensing area 144. While at the dispensing area 144, the central processor 20 coordinates the movement of the platform 74 and the docking fixture 170 with operation of the reagent dispensing source 146 to introduce reagent into one or more specimen-containing wells.

The docking fixture 170 releases the nozzle 148 after dispensement of reagent. More particularly, the carrier 24 returns the nozzle 148 to the holder 160 and there releases the docking fixture 170. This mode of operation frees the carrier 24 for other transport functions within the system 10, while the nozzle 148 lays at rest within its holder 160.

Various constructions are possible. In the illustrated embodiment, the docking fixture 170 is attached to the movable head 116 of the fluorescence reader 98. Operation of the fifth stepper motor 120 moves the docking fixture 170 along the horizontal track 118 above the tray platform 74.

The illustrated embodiment employs magnetism to releasably engage the docking fixture 170 to the nozzle 148. In this arrangement, the docking fixture 170 carries a permanent rare earth magnet 174. The nozzle 148 includes a surface 172 that nests within the fixture 170. The mating surface 172 includes material that is attracted by the magnet 174 the fixture 170 carries. Alternatively, the mating surface 172 could carry another rare earth magnet.

The central processor 20 coordinates the operation of the first, second, and third stepper motors 54, 68, and 78 to engage a selected specimen tray 12 on the platform 74 within the main incubation region 34 of the system 10. To transport the engaged tray 12 to the reagent dispensing region 40, the central processor 20 moves the platform 74 into its fully retracted position within the carrier frame 64. The central processor 20 then moves the carrier 24 vertically downward into the reagent dispensing region 40 (as FIG. 19 shows). At this time, the nozzle 148 rests in a locked condition within the holder 160 (i.e., the latch solenoid 168 is not energized). The docking fixture 170 moves downward and nests with the nozzle surface 172 (as FIG. 20 shows). The nesting fixture 170 magnetically engages the nozzle surface 172.

Figure 21:
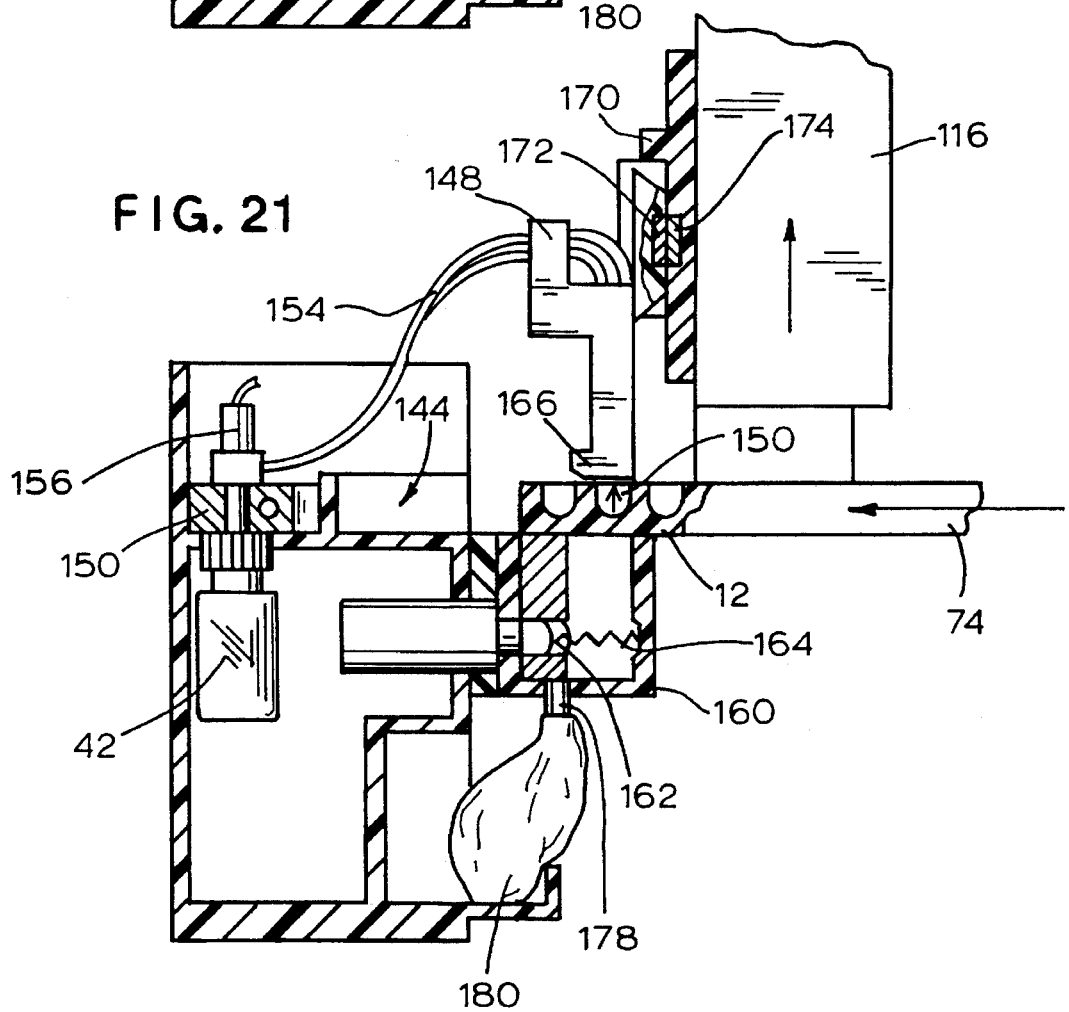
FIG. 21 is an enlarged side section view of the reagent dispensing nozzle, its holder, and the associated docking fixture shown in FIG. 18, with the docking fixture engaged with the nozzle and transporting the nozzle to the fluid dispensing area of the system shown in FIG. 1.

The central processor 20 energizes the solenoid 168 to withdraw the latch 162, freeing the nozzle 148 within the holder 160. The central processor 20 moves the carrier 24 vertically upward. The fixture 170 lifts the magnetically engaged nozzle 148 from the holder 160 and into the reagent dispensing area 144 (as FIGS. 21 shows).

Figure 22:
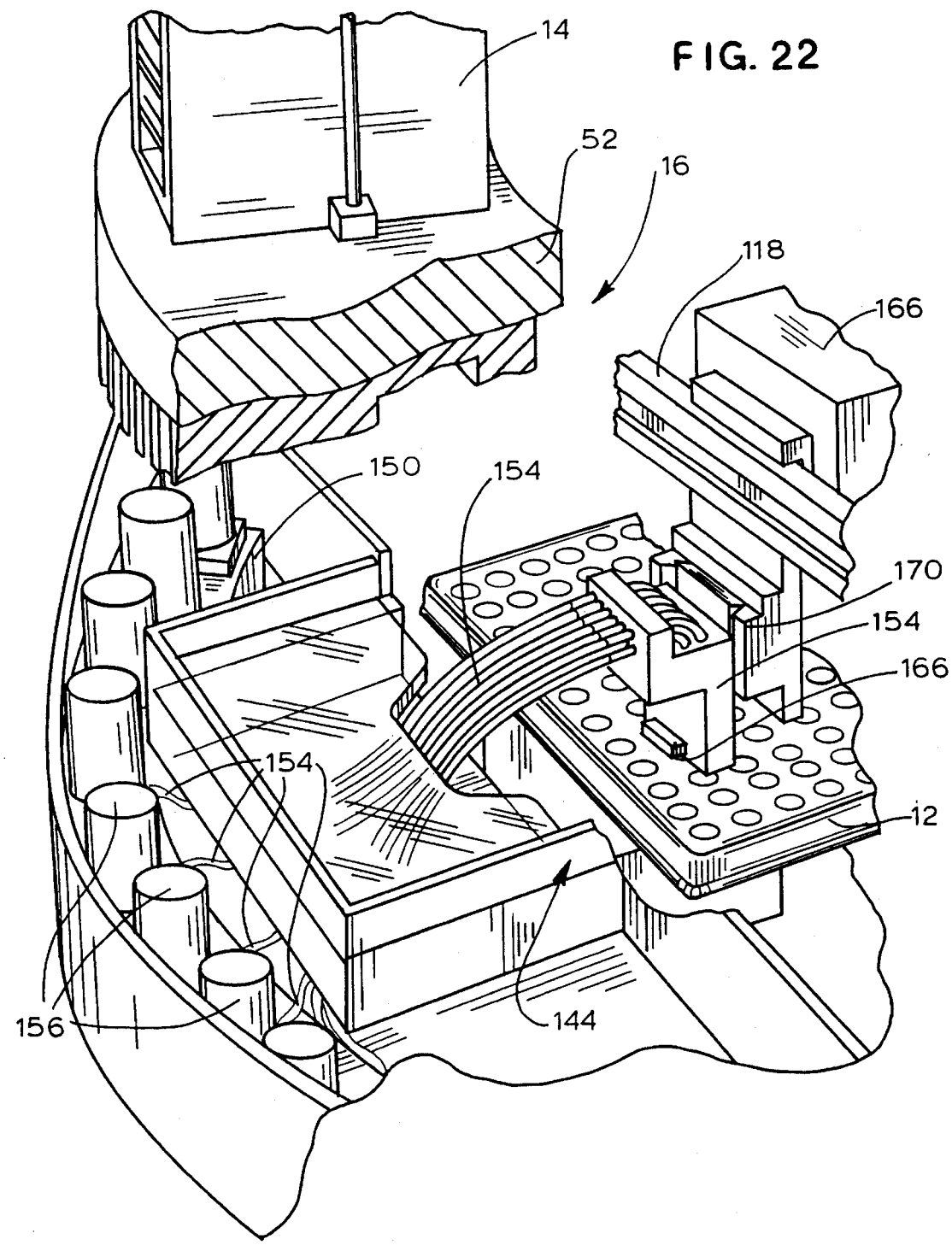
FIG. 22 is a perspective view showing the manipulation of the reagent dispensing while releasably attached to the docking fixture at the fluid dispensing area of the system.

As FIG. 22 shows, the central processor 20 then operates the third stepper motor 78 to move the tray-carrying platform 74 out of the carrier frame 64 into the fluid dispensing area 144. By coordinating the operation of the third and fifth stepper motors 78 and 120, the central processor 20 horizontally positions a row of the specimen tray 12 beneath the nozzle 148 while it transversely positions the nozzle 148 along this row to bring the desired specimen well 48 under the desired reagent dispensing port 158. The central processor 20 then opens the solenoid valve 156 associated with the vial 42 for the desired reagent to dispense a predetermined aliquot of the desired reagent into the selected well 48.

The central processor 20 positions the nozzle 148 engaged by the movable fixture 170 by dead reckoning. The processor 20 measures the position of the fixture 170 along the track 118 in steps sent to the fifth stepper motor 120 from the fixture's home position.

The drive system of the stepper motor 120 is calibrated using the fluorometer located within the transport head 116, which also carries the fixture 170. The system start-up routine includes an initialization process that uses an onboard encoder bar 224 and an optical interrupter 226. As FIGS. 5 and 6 best show, the optical interrupter 226 is carried on the movable head 116 of the fluorescence reader 98 behind the belt drive 122. The encoder bar 224 is also carried on the platform 74 behind the belt drive 122.

The encoder bar 224 includes a series of spaced apart teeth 228 sandwiched between the optical interrupter 226 along its path of movement. The centerlines of the teeth 228 mark the centerline positions of the tray wells 48 when the tray 12 is present on the platform 64.

As the head 116 travels along the track 118, the optical interrupter 226 scans the encoder bar 224. The teeth 228 block light transmission through optical interrupter 226. The spacing between the teeth 228 allows light transmission through the optical interrupter 224. Thus, as it travels along the bar 224, the interrupter 224 senses sequential conditions of light and no light. By correlating the sensed conditions of no light (i.e., the position of the teeth 228) to the measured steps of the motor 120, the central processor 20 establishes a table of well stop positions. The central processor 20 uses this table to guide the centerline of the nozzle 148 to a particular well 48 during reagent dispensing operations. Additional incremental stepping actions of the motor 78 and the motor 120 under the control of the central processor 20 align the selected nozzle port 158 over the selected well 48.

After dispensing reagent, the central processor 20 moves the tray-carrying platform 74 into its fully retracted position. The central processor 20 vertically lowers the carrier 24 to return the nozzle 148 to its holder 160. The solenoid 168 is not energized, and the spring-biased latch 162 snaps into locking engagement with the nozzle tab 166.

The central processor 20 moves the carrier 24 vertically upward. The magnet attraction holding the nozzle surface 172 to the fixture 170 is such that vertical movement of the carrier 24 while the nozzle 148 is locked within the holder 160 overcomes the force of the magnetic coupling, separating the nozzle surface 172 from the docking fixture 170. The carrier 24 is thereby freed to return the engaged specimen tray 12 (now with added reagent) back to the main incubation region 34 for further processing.

It should be appreciated that other releasable attachment techniques could be used to dock the nozzle 148 to the fixture 170 for transport. For example, an electromagnetic coupling arrangement could be employed, as could various electro-mechanical coupling arrangements.

Figure 23:
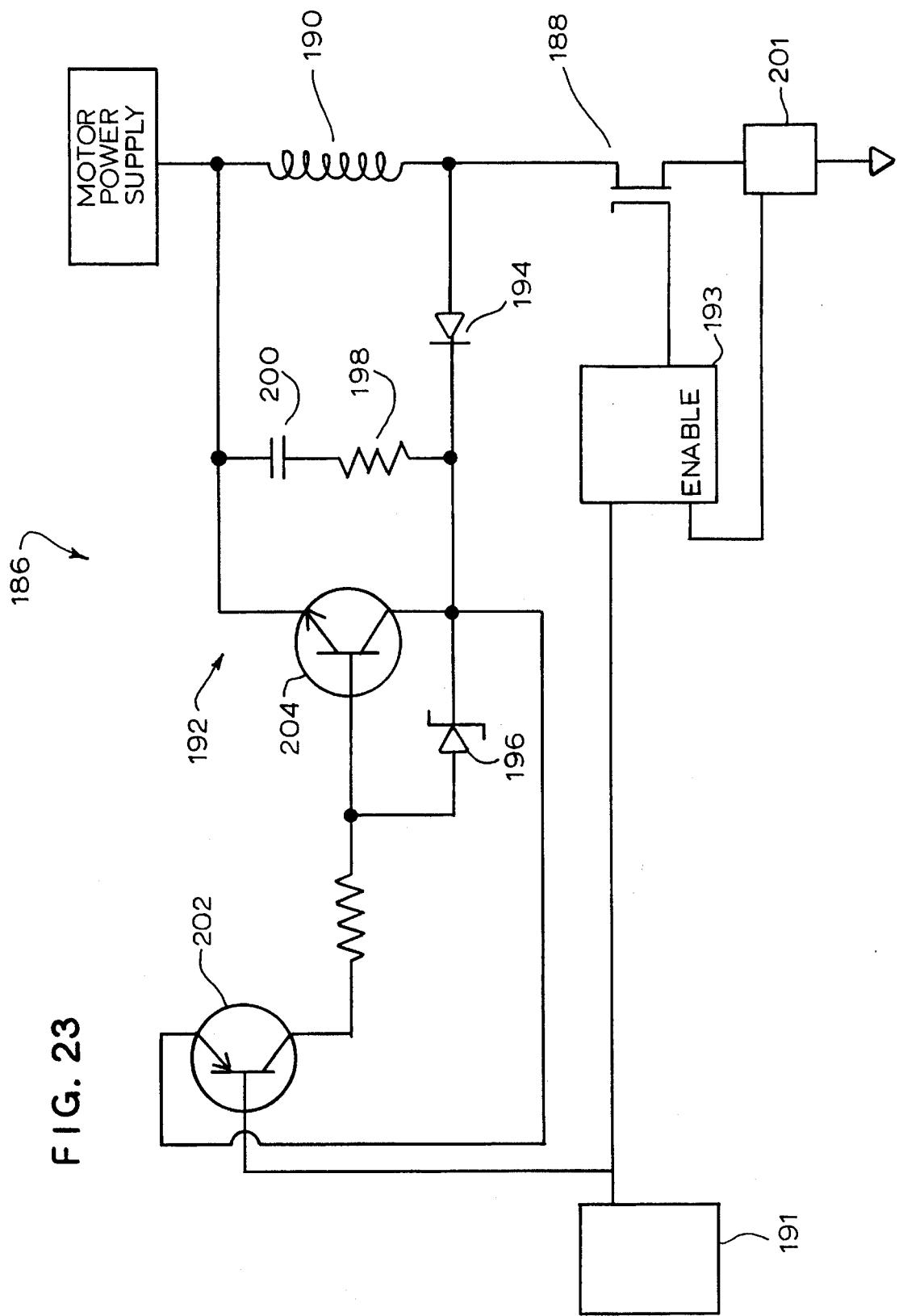
FIG. 23 is a schematic view of a stepper motor control circuit associated with the system shown in FIG. 1.

The central processor 20 includes a motor driver system 186 (see FIG. 23) for controlling the stepper motors 54; 68; 78; 112; and 120 associated with the system 10. The system 186 includes a conventional field effect transistor (FET) 188 connected in series with the motor coil 190. A phase controller 191 controls voltage to the FET 188, by that controlling its phase of operation. In an on phase, the controller 191 supplies voltage to the FET 188. This allows current to flow through the coil 190. In an off phase, the controller 191 supplies no voltage to the FET 188. This interrupts current flow through the coil 190.

Although not shown, the associated stepper motor includes a rotor and two or more coils 190 under the control of the controller 191. The controller 191 successively supplies current to the coils 190 to step the motor rotor to its successive operating positions.

A FET controller 193 provides either a true or not true enable signal that switches the FET 188 for the coil 190 between an on state (when true) and an off state (when not true). When current is applied to the coil 190 (i.e., during its on phase of operation), the chop controller 201 rapidly switches the FET 188 between its on and off states, modulating the current and keeping it from rising above the nominal motor current (for example, 5 amps). The current rises and falls as the FET 188 switches on and off, creating a conventional unipolar chopping mode drive effect. In the chopping mode, the FET 188 keeps the average current in the coil 190 from rising above the nominal, relatively low motor current, despite a relatively high applied voltage (for example, 40 volts).

The system 186 also includes a flyback circuit 192 for each motor coil 190. The flyback circuit 192 includes a conventional steering diode 194 and a conventional zener-diode 196. When the FET 188 is turned off, the steering diode 194 is forward biased to normally conduct current from the coil 190. The zener-diode 196 is connected in the reverse bias direction. The zener-diode 196 thus normally resists flow of current in the direction through the steering diode 194, until its breakdown Voltage is reached.

The flyback circuit 192 also includes a conventional snubber circuit, consisting of series resistor 198 and capacitor 200.

The flyback circuit 192 further includes two conventional bipolar transistors 202 and 204. The first transistor 202 is a PNP-type whose base is connected to the coil controller 191. The first transistor 202 acts as a switch under the control of the coil controller 191. The first transistor 202 conducts current (a switched closed state) when current is supplied to the coil 190 (during its on phase of operation). The first transistor 202 does not conduct current (a switched opened state) when no current is supplied to the coil 190 (during its-off phase of operation).

The second transistor 204 is an NPN-type. Its base to emitter voltage is selectively biased to two different voltages, one high and the other low, depending upon a phase of operation of the coil 190. The bias voltage, in turn, affects the overall dissipation of power through the flyback circuit 192.

More particularly, the collector of the second transistor 204 is connected to the steering diode 194 to conduct current from the coil 190. The emitter of the second transistor 204 is connected to the coil 190 to return this current to the coil 204, minus any energy dissipated by the transistor 204.

The base of the second transistor 204 is connected to the collector of the first transistor 202. The collector of the second transistor 204 is connected to the emitter of the first transistor 202 between the steering diode 194 and the zener-diode 196. The zener-diode 196 is connected in the reverse biased direction (during the off phase of the controller 191) between the collector and base of the second transistor 204.

The coil 190 will dissipate retained stored energy into the flyback circuit 192 whenever the FET 188 interrupts current flow through the coil 190 (i.e., when the FET 188 is switched off while the controller 191 operates the coil 190 in its on phase mode). The coil 190 also will dissipate retained stored energy into the flyback circuit 192 whenever current to the coil 190 itself terminates (i.e., when the controller 191 switches operation from the on phase. mode to the off phase mode).

The FET 188 repeatedly interrupts current flow through the coil 191 at short intervals while the motor coil 190 operates in its chopping mode. Whenever the FET 188 switches off (when the controller 193 provides a "not true" enable signal) energy discharged by the coil 190 enters the flyback circuit 192.

In these circumstances, the coil 190 is in its on phase. The coil controller 191 biases the base of the first transistor 202 to a switched closed state. The first transistor 202 conducts current at a first voltage, which is less than the breakdown voltage of the zener-diode 196. The current in the flyback circuit 192 flows through the steering diode 194 and through the path of least electrical resistance, which is through the first transistor 202. The zener-diode 196 operates below its breakdown voltage in its reverse direction to block current flow in its path.

The current flows through the first transistor 202 to the base of the second transistor 204. The first transistor 202 biases the base emitter junction of the second transistor 204 at the first, relatively low voltage. Preferably, the first voltage is generally about 2 volts.

In this low voltage mode, the flyback circuit 192 recirculates current through the second transistor 204 with little dissipation during the intervals while the FET 188 is switched off. This sustains a smooth, constant torque while the coil 190 is energized (i.e., receiving voltage) and operating in its chopping mode. Due to the low voltage mode of the flyback circuit 192, the stepper motor provides steady, sustained power.

When it is time to transfer voltage to a successor coil in the motor, the controller 191 switches the coil 190 to its off phase When its current supply is interrupted, the coil 190 again discharges its energy into the flyback circuit 192 (the enable signal transmitted to the FET 188 has no effect once the controller 191 operates in its off phase). Since the coil 190 is now in its off phase, the first transistor 202 is in its switched open state and does not conduct current.

Instead, the current flows through the steering diode 194 directly into the path of the zener-diode 196. The reverse current is such that the zener-diode 196 quickly reaches its breakdown voltage. The zener-diode 196 then conducts current to bias the second transistor 204 at a second voltage, which is the breakdown voltage of the zener-diode 196. Preferably, the second voltage is generally about 180 volts.

In this high voltage mode, the flyback power quickly dissipates the energy stored in the coil 190. This rapid dissipation of energy provides a smooth and quick transition of voltage to the successor coil. The high voltage mode of the flyback circuit 192 provides sustained speed to the stepper motor.

The description of the system 10 in the illustrated embodiments is not intended to limit the scope of the invention to the particular types of analytical systems or particular type of analytical techniques disclosed in this specification. The system 10 that embodies the invention can be used to conduct different analyzes, besides the microbiotic susceptibility procedures described. It will be seen and appreciated that the invention is applicable for use with diverse analytical types and techniques, though they are not all described in detail in this application.

The features and advantages of the various aspects of the invention are set forth in the claims that follow.

We claim:

1. A system for processing a specimen to which fluid must be added comprising:

a housing, a first work station in said housing including plural sources of fluid to be added to a specimen, a fluid dispensing area for receiving the specimen, a nozzle having plural fluid dispensing ports, each fluid dispensing port individually and continuously communicating with a respective one of said plural sources of fluid for dispensing the fluids to the specimen, and valving means for selectively controlling flow of said fluids from said sources to the specimen via said plural fluid dispensing ports of said nozzle, carrier means movable in said housing, said carrier means being operable for movement in said first work station during fluid dispensing operations and for movement outside said first work station to perform a different processing function, controller means for selectively controlling the operation of said carrier means, and cooperating coupling means on said nozzle and said carrier means, said cooperating coupling means being operative for attaching said nozzle to said carrier means when said carrier means moves in said first work station to transport said nozzle to said fluid dispensing area of said first work station, said cooperating coupling means being operative also for releasing said nozzle from said carrier means preparatory to said carrier means moving outside said first work station out of association with said nozzle.

2. A system according to claim 1 and further including a second work station for performing a processing function on the specimen, and wherein, said carrier means participates in said performing of the processing function at said second work station.

3. A system according to claim 2 wherein said second work station comprises detecting means for assaying for a certain material in the specimen, and wherein, said carrier means transports the specimen to said detecting means.

4. A system according to claim 2 wherein said second work station comprises means for incubating the specimen, and wherein, said carrier means transports the specimen to and from said incubating means.

5. A system according to claim 1 wherein, said carrier means also transports the specimen to said fluid dispensing area.

6. A system according to claim 1 and further including a second work station for performing a processing function on the specimen, wherein, said carrier means transports the specimen to said fluid dispensing area of said first work station in association with said nozzle, and wherein, said carrier means transports the specimen to said second work station out of association with said first work station and said nozzle.

7. A system according to claim 6 wherein said second work station includes means for incubating the specimen.

8. A system according to claim 6 wherein said second work station comprises means for assaying for a certain material in the specimen.

9. A system according to claim 1 wherein said carrier means includes means for transporting the specimen.

10. A system according to claim 1 wherein said carrier means includes a frame and means for holding the specimen on said frame for transport.

11. A system according to claim 10 wherein said carrier means includes means for moving the held specimen relative to said frame.

12. A system according to claim 10 wherein said carrier means includes means for moving the held specimen on said frame between a first position within said frame and a second position outside of said frame.

13. A system according to claim 10 wherein said carrier means includes means for moving said nozzle relative to said frame while said nozzle is attached to said carrier means.

14. A system according to claim 1 wherein said carrier means includes means for moving said nozzle while said nozzle is attached to said carrier means.

15. A system according to claim 1 wherein said first work station includes a holder for said nozzle, and wherein said cooperating coupling means, when attaching said nozzle to said carrier means, moves said nozzle out of said holder preparatory to dispensing said fluid to the specimen and returns said nozzle to said holder preparatory to said carrier means moving outside said work station.

16. A system according to claim 15 wherein said holder includes latching means operative between an engaged position with said nozzle, locking said nozzle within said holder; and a disengaged position with said nozzle, freeing said nozzle for removal from said holder.

17. A system according to claim 16 wherein said controller means moves said latching means to said disengaged position preparatory to said carrier means removing said nozzle from said holder; and moves said latching means to said engaged position when said carrier means returns said nozzle to said holder.

18. A system according to claim 15 wherein said holder includes means for introducing a washing fluid into said holder and onto said nozzle, thereby to wash said nozzle.

19. A system for processing a specimen to which one or more fluids must be added comprising:

a housing, a work station in said housing including a source of plural fluids to be added to a specimen, a fluid dispensing area for receiving the specimen, and a nozzle having plural fluid dispensing ports communicating individually with a respective one of said plural fluids of said source for dispensing said plural fluids, carrier means movable in said housing, said carrier means being operable for movement in said work station during fluid dispensing operations and for movement outside said work station to perform a different processing function, controller means for selectively controlling the operation of said carrier means, and cooperating magnetic coupling means on said nozzle and said carrier means, said cooperating coupling means being operative for magnetically attaching said nozzle to said carrier means when said carrier means is in said work station to transport said nozzle to said fluid dispensing area of said work station, said coupling means being operative for breaking said magnetic attachment preparatory to said carrier means moving outside said work station out of association with nozzle.

20. A system according to claim 19 wherein said work station includes a holder for said nozzle, and wherein said coupling means, when attached to said nozzle, moves said nozzle out of said holder for dispensing fluid to the specimen, and returns said nozzle to said holder before said carrier means moves outside said work station.

21. A system according to claim 20 wherein said holder includes latching means operative between an engaged position with said nozzle, locking said nozzle within said holder; and a disengaged position with said nozzle, freeing said nozzle for removal from said holder, and wherein, when said nozzle is magnetically attached to said carrier means and is locked by said latching means within said holder, movement of said carrier means away from said holder breaks said magnetic attachment between said nozzle and said carrier means.

22. A system according to claim 21 wherein said controller means moves said latching means to said disengaged position preparatory to said carrier means moving said nozzle out of said holder, and moves said latching means to said engaged position when said carrier means returns said nozzle to said holder.

23. A system according to claim 19 wherein said holder includes means for washing said nozzle within said holder.

24. A system for processing plural specimens each disposed individually in a respective well of a processing tray having plural such wells, and to which specimens selected fluids must be added individually, said system processing plural such trays, said system comprising:

a housing;

a work station in said housing, said work station including:

a fluid dispensing area for receiving a processing tray holding plural specimens each in a respective one of plural wells of the processing tray, plural sources of fluid to be added to selected ones of the plural specimens by discharge from a respective dispensing port into a selected respective one of the plural wells of the processing tray, a durable and reusable nozzle having plural fluid dispensing ports, each fluid dispensing port of said plural fluid dispensing ports individually and continuously communicating with a respective one of said plural sources of fluid for dispensing the fluid individually to a specimen, and plural valving means for selectively controlling flow of said fluids individually from said plural sources to the specimens via said plural fluid dispensing ports of said nozzle;

carrier means movable in said housing, said carrier means being operable for movement in said work station during fluid dispensing operations and for movement outside said work station to perform a different processing function;

controller means for selectively controlling the operation of said carrier means; and cooperating coupling means on said nozzle and said carrier means, said cooperating coupling means being operative for selectively removably attaching said nozzle to said carrier means when said carrier means moves into said work station to transport said nozzle to said fluid dispensing area of said work station, said cooperating coupling means being operative also for selectively releasing said nozzle from said carrier means preparatory to said carrier means moving outside said work station out of association with said nozzle;

wherein said work station includes a holder for said nozzle; and wherein said cooperating coupling means, when attaching said nozzle to said carrier means, moves said nozzle out of said holder preparatory to dispensing said fluid to the specimen; and said cooperating coupling means returns said nozzle to said holder preparatory to said carrier means moving outside said work station;

wherein said holder includes latching means operative between an engaged position with said nozzle, locking said nozzle within said holder; and a disengaged position with said nozzle, freeing said nozzle for removal from said holder by said cooperating coupling means.

25. A system according to claim 24 wherein said carrier means includes means for transporting a processing tray to and from said work station.

26. A system according to claim 25 further including another work station which includes detecting means for assaying a specimen for a certain material in the specimen, and said carrier means transports the specimen in a processing tray outside of said work station to said another work station and to said detecting means.

27. A system according to claim 25 further including another work station which includes means for incubating a specimen in a processing tray, and said carrier means transports the specimen in the processing tray to and from said incubating means, and between said work station and said another work station.

28. A system according to claim 24 wherein said carrier means includes a frame and means for holding a processing tray on said frame for transport.

29. A system according to claim 28 wherein said carrier means further includes means for moving the held processing tray along a respective axis relative to said frame.

30. A system according to claim 29 wherein said carrier means includes means for moving said nozzle, while said nozzle is attached to said carrier means, along a respective axis which is perpendicular to the axis along which said processing tray is movable relative to said frame.

31. A system according to claim 30 wherein said means for moving the held processing tray of said carrier means includes means for moving the held processing tray on said frame between a first position and a second position, said first position being within said frame so that in said first position said processing tray is movable relative to a detecting means for assaying a specimen within any selected well of said processing tray for a certain material in the specimen; and said second position being partially or fully outside of said frame, in said second position of said processing tray said processing tray being selectively movable relative to said nozzle and said plural fluid dispensing ports thereof so that fluid is dischargeable from any one of said plural fluid dispensing ports into any one of the plural wells of said processing tray and to the specimen therein in conjunction with selected movement of said nozzle relative to said frame by said means for moving said nozzle; also in said second position said processing tray being extended outside of said frame and being removable from said carrier means to another work station which includes means for incubating a specimen in a processing tray.

32. A system according to claim 24 wherein said controller means also moves said latching means to said disengaged position preparatory to said carrier means removing said nozzle from said holder; and moves said latching means to said engaged position when said carrier means returns said nozzle to said holder.

33. A system according to claim 24 wherein said holder includes means for introducing a washing fluid into said holder and onto said nozzle, thereby to wash said nozzle.

* * * * *